United States Patent
Kim et al.

(10) Patent No.: US 9,867,582 B2
(45) Date of Patent: Jan. 16, 2018

(54) APPARATUS AND METHOD FOR CONTROLLING X-RAY RADIATION FIELD OF X-RAY IMAGING APPARATUS

(71) Applicant: SAMSUNG ELECTRONICS CO., LTD., Suwon-si (KR)

(72) Inventors: Jong-pil Kim, Yongin-si (KR); Woo-sup Han, Yongin-si (KR)

(73) Assignee: SAMSUNG ELECTRONICS CO., LTD., Suwon-si (KR)

(*) Notice: Subject to any disclaimer, the term of this patent is extended or adjusted under 35 U.S.C. 154(b) by 0 days.

(21) Appl. No.: 14/315,734

(22) Filed: Jun. 26, 2014

(65) Prior Publication Data

US 2015/0003588 A1 Jan. 1, 2015

(30) Foreign Application Priority Data

Jun. 26, 2013 (KR) .................. 10-2013-0074059

(51) Int. Cl.
*A61B 6/08* (2006.01)
*A61B 6/03* (2006.01)
*A61B 6/00* (2006.01)
*H01J 35/16* (2006.01)

(52) U.S. Cl.
CPC ............ *A61B 6/08* (2013.01); *A61B 6/032* (2013.01); *A61B 6/4014* (2013.01); *A61B 6/4071* (2013.01); *A61B 6/502* (2013.01); *H01J 35/16* (2013.01)

(58) Field of Classification Search
CPC ................................. A61B 6/08; A61B 6/587
See application file for complete search history.

(56) References Cited

U.S. PATENT DOCUMENTS

| | | | |
|---|---|---|---|
| 6,480,565 B1 | 11/2002 | Ning | |
| 7,359,484 B2 | 4/2008 | Qiu et al. | |
| 7,388,940 B1* | 6/2008 | De Man | A61B 6/032 378/4 |
| 7,431,500 B2 | 10/2008 | Deych et al. | |
| 7,496,176 B2 | 2/2009 | Aslund | |
| 7,864,917 B2 | 1/2011 | Ribbing et al. | |
| 7,978,816 B2 | 7/2011 | Matsuura et al. | |
| 7,991,120 B2 | 8/2011 | Okunuki et al. | |
| 2007/0165781 A1 | 7/2007 | Aslund | |

(Continued)

FOREIGN PATENT DOCUMENTS

KR 10-0933118 B1 12/2009
KR 10-2012-0108843 A 2/2012

*Primary Examiner* — Hoon Song
(74) *Attorney, Agent, or Firm* — Sughrue Mion, PLLC

(57) ABSTRACT

An apparatus is provided for controlling an X-ray radiation field of an X-ray imaging apparatus including an X-ray generator and an X-ray detector arranged opposite to the X-ray generator. The apparatus includes a light-emitting unit configured to emit light and disposed adjacent to one of the X-ray generator and the X-ray detector, a light-receiving unit configured to detect the light emitted by the light-emitting unit and disposed adjacent to the other one of the X-ray generator and the X-ray detector, a radiation field setter configured to set an X-ray radiation field based on the detected light, and an X-ray driver configured to control driving of the X-ray generation units which correspond to the set X-ray radiation field, to emit an X-ray.

20 Claims, 26 Drawing Sheets

(56) References Cited

U.S. PATENT DOCUMENTS

| | | | |
|---|---|---|---|
| 2009/0154153 A1* | 6/2009 | Lin | F21K 9/00 |
| | | | 362/231 |
| 2011/0069808 A1 | 3/2011 | Defreitas et al. | |
| 2011/0075809 A1 | 3/2011 | Boese et al. | |
| 2012/0008739 A1 | 1/2012 | Hoernig et al. | |
| 2014/0056401 A1* | 2/2014 | Harada | A61B 6/08 |
| | | | 378/4 |

* cited by examiner

APPARATUS AND METHOD FOR CONTROLLING X-RAY RADIATION FIELD OF X-RAY IMAGING APPARATUS

CROSS-REFERENCE TO RELATED APPLICATION

This application claims priority from Korean Patent Application No. 10-2013-0074059, filed on Jun. 26, 2013, in the Korean Intellectual Property Office, the disclosure of which is incorporated herein in its entirety by reference.

BACKGROUND

1. Field

Apparatuses and methods consistent with exemplary embodiments relate to an X-ray imaging.

2. Description of the Related Art

Cancer can be diagnosed from an X-ray image obtained by a diagnostic X-ray apparatus which transmits an X-ray through a human body and determines cancer cells from an X-ray image. In the related art X-ray apparatus, a portion of a patient's body to be imaged is positioned on or proximate to a flat panel detector (FPD). The imaging is performed by varying a distance between an X-ray radiation source and a detector, and varying radiation conditions according to the area to be imaged. To reduce the dispersion of a radiated X-ray and a patient's exposure to radiation, a collimator is arranged in front of an X-ray radiation source to control an X-ray radiation field. An X-ray is radiated from a single source, for example, a thermal negative electrode type X-ray tube, and the X-ray having passed through the patient is sensed by the FPD. The detected X-ray is converted into electrical signals, which are image-processed and output as an X-ray image. According to the above process, a two-dimensional (2D) image sheet may be obtained and read.

In a related art X-ray system using a cone beam type X-ray source and an FPD, an X-ray radiation field is controlled by adjusting a distance between the source and the detector according to an imaging range. Accordingly, a patient's exposure to radiation increases and scattering also further increases exposure to radiation and deteriorates the quality of an image. Although a line scan type detector and a dual collimator may be employed to reduce the patient's exposure to radiation, lots of time is spent to obtain an entire image of an image object. Also, an image captured by the related art X-ray system is a 2D image, and thus, there is a limitation of not knowing depth information.

Additionally, according to a related art technology for a breast X-ray, the breast of a patient is placed on a support and compressed by a compression paddle to a maximum degree, and then an image area of a compressed breast is captured.

To reduce an X-ray dose and obtain a superior image, the breast of a patient is compressed with a great force so that the breast is substantially flattened out and the thickness of the breast is substantially decreased. As a result, a patient usually feels much pain and/or discomfort during the breast mammography. Also, since the related art X-ray breast mammography is performed at least four times corresponding to a left mediolateral oblique (LMLO) view, a right mediolateral oblique (RMLO) view, a left craniocaudal (LCC) view, and a right craniocaudal (RCC) view in the same imaging session, an amount of the pain of a patient increases and the patient's radiation dose increases. Furthermore, when there are abnormality findings in an image, enlargement imaging and tomography may be additionally performed, which increases the pain and the radiation dose of a patient. Also, a workflow may be increased.

SUMMARY

One or more embodiments of the present invention include an X-ray photography device and method which may reduce unnecessary radiation dose of a patient by reducing a distance between an X-ray generator and an X-ray detector.

According to an aspect of an exemplary embodiment, there is provided an apparatus for controlling an X-ray radiation field of an X-ray imaging apparatus including an X-ray generator and an X-ray detector arranged opposite to the X-ray generator, the apparatus including a light-emitting unit configured to emit light and disposed adjacent to one of the X-ray generator and the X-ray detector, a light-receiving unit configured to detect the light emitted by the light-emitting unit and disposed adjacent to the other one of the X-ray generator and the X-ray detector, a radiation field setter configured to set an X-ray radiation field based on the detected light, and an X-ray driver configured to control driving of the X-ray generation units which correspond to the set X-ray radiation field, to emit an X-ray.

The X-ray generator may include X-ray generation units that are linearly arranged, and the light-emitting unit may include light-emitting elements that are arranged in a same direction as a direction in which the X-ray generation units are linearly arranged.

The light-emitting elements may include at least of a light-emitting diode, an organic light-emitting diode, a laser diode, and a lamp.

The light-emitting elements may emit at least one of visible rays and infrared rays.

The X-ray generator may include X-ray generation units that are linearly arranged, and the light-receiving unit may have a linear light detection surface extending in a same direction as a direction in which the X-ray generation units are linearly arranged.

The X-ray generator may include X-ray generation units that are linearly arranged, and the light-receiving unit may include light-receiving elements that are arranged in a same direction as a direction in which the X-ray generation units are linearly arranged.

The light-receiving elements may include at least one of a photodiode, a phototransistor, and an image sensor.

The light-emitting unit may be provided at a side surface of one of the X-ray generator and the X-ray detector, and the light-receiving unit may be provided at a side surface of the other one of the X-ray generator and the X-ray detector.

The light-emitting unit may be attached to a side surface of the X-ray generator, the side surface being a leading surface with respect to a rotation direction in which the X-ray generator and the X-ray detector rotate.

The light-receiving unit may be attached to a side surface of the X-ray detector, the side surface being a leading surface with respect to a rotation direction in which the X-ray generator and the X-ray detector rotate.

According to an aspect of another exemplary embodiment, there is provided a method of controlling an X-ray radiation field of an X-ray imaging apparatus including an X-ray generator and an X-ray detector arranged opposite to the X-ray generator, the method including emitting light from a light-emitting unit disposed adjacent to one of the X-ray generator and the X-ray detector toward the other one of the X-ray generator and the X-ray detector, detecting the emitted light using a light-receiving unit disposed adjacent to the other one of the X-ray generator and the X-ray detector, setting an X-ray radiation field based on the detected light, and controlling driving of only the X-ray generation units which correspond to the set X-ray radiation field, to emit an X-ray.

The X-ray generator may include X-ray generation units that are linearly arranged, and the emitting the light may include emitting a linear light having a linear beam section that extends continuously or discontinuously in a same direction as a direction in which the X-ray generation units are linearly arranged.

The setting the X-ray radiation field may include setting the X-ray radiation field as an area obtained by adding a preset width to an outer edge, to extend the X-ray radiation field into an area where the light is not detected.

The X-ray generator may include X-ray generation units that are linearly arranged and the method may further include rotating the X-ray generator and the X-ray detector, which face each other, around a rotational axis that is between the X-ray generator and the X-ray detector and parallel to a direction in which the X-ray generation units are linearly arranged.

The light-emitting unit may be attached to a side surface of the X-ray generator, the side surface being a leading surface in a rotation direction in which the X-ray generator and the X-ray detector rotate, and configured to emit light prior to emission of the X-ray by the X-ray generator.

The light-receiving unit may be attached to a side surface of the X-ray detector, the side surface being a leading surface in a rotation direction in which the X-ray generator and the X-ray detector rotate, and configured to receive light prior to detection of the X-ray by the X-ray detector.

Additional aspects will be set forth in part in the description which follows and, in part, will be apparent from the description, or may be learned by practice of the presented embodiments.

BRIEF DESCRIPTION OF THE DRAWINGS

The above and/or other aspects will become more apparent by describing certain exemplary embodiments with reference to the accompanying drawings, in which.

DETAILED DESCRIPTION

Figure 1:
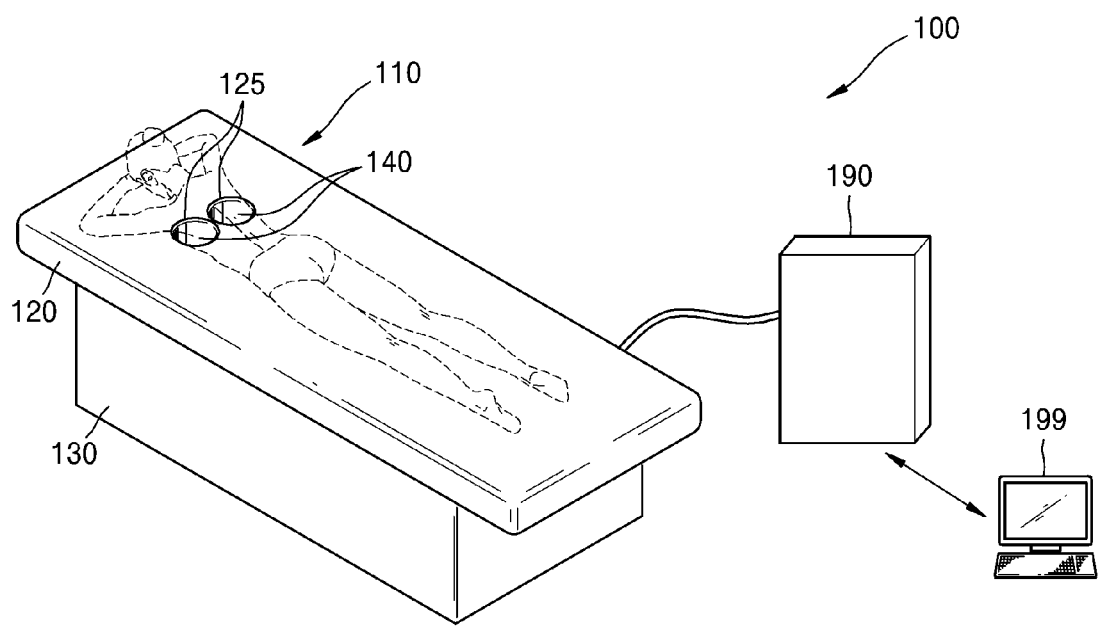
FIG. 1 is a schematic perspective view of an X-ray imaging apparatus according to an exemplary embodiment.

Certain exemplary embodiments are described in greater detail below with reference to the accompanying drawings.

In the following description, like drawing reference numerals are used for the like elements, even in different drawings. The matters defined in the description, such as detailed construction and elements, are provided to assist in a comprehensive understanding of exemplary embodiments. However, exemplary embodiments can be practiced without those specifically defined matters. Also, well-known functions or constructions are not described in detail since they would obscure the application with unnecessary detail.

When a part may "include" a certain element, unless specified otherwise, it may not be construed to exclude another element but may be construed to further include other elements. The terms such as "~ portion", "~ unit", and "~ module", stated in the specification may signify a unit to process at least one function or operation and the unit may be embodied by hardware, software, or a combination of hardware and software.

An image may signify multi-dimensional data formed of discrete image elements, for example, pixels in a two-dimensional (2D) image and voxels in a three-dimensional (3D) image. For example, an image may include an X-ray image, a computed tomography (CT) image, a magnetic resonance imaging (MRI) image, an ultrasound image, and any medical image of an object that is acquired by other medical imaging apparatus.

An object may include a human, an animal, or a part of a human or an animal. For example, an object may include organs such as the liver, the heart, the womb, the brain, a breast, the abdomen, etc., or blood vessels. Also, an object may include a phantom that signifies matter having a volume that is approximately the intensity and effective atomic number of a living thing, and may include a sphere phantom having a property similar to a human body.

A user may be a medical doctor, a nurse, a clinical pathologist, a medical imaging expert, a technician who fixes a medical apparatus, etc., but an exemplary embodiment is not limited thereto.

Expressions such as "at least one of," when preceding a list of elements, modify the entire list of elements and do not modify the individual elements of the list.

FIG. 1 is a schematic perspective view of an X-ray imaging apparatus 100 according to an exemplary embodiment. Referring to FIG. 1, the X-ray imaging apparatus 100 may include a main assembly 110 and a control apparatus 190 for controlling X-ray imaging and processing an X-ray image. In the X-ray imaging apparatus 100, a user may manipulate the control apparatus 190 and display a generated X-ray image on a console 199 that is externally provided. Although FIG. 1 illustrates that the control apparatus 190 is separate from the main assembly 110 and connected thereto in a wired manner, an exemplary embodiment is not limited thereto. In another exemplary embodiment, the control apparatus 190 may be integrally formed with the main assembly 110. Also, some elements of the control apparatus 190 may be embodied by an external device capable of communicating in a wireless manner.

The main assembly 110 includes a table 120 for a patient, a support 130 supporting the table 120, and a holder assembly 140. Two through-holes 125, where both breasts may be disposed when a patient lies on her stomach on the table 120, are formed in the table 120. One holder assembly 140 is provided in each of the through-holes 125. The holder assembly 140 is where either breast, i.e., the object, is placed and where X-ray imaging is performed.

The diameter of each of the through-holes 125 of the table 120 is equal to or greater than the outer diameter of the holder assembly 140 so that the holder assembly 140 may move within a corresponding one of the through-holes 125. For example, the holder assembly 140 may be detachably coupled to an upper plate of the table 120. Since the position or size of the object varies according to individual patients, the position of the holder assembly 140 is set to be optimal to a patient so that the patient may experience X-ray imaging at a comfortable posture. It is unnecessary to provide both holder assemblies 140 to be capable of moving with respect to the table 120. For example, while only one holder assembly 140 may be provided to be capable of moving with respect to the table 120, the other holder assembly 140 may be fixedly provided on the table 120.

Figure 2:
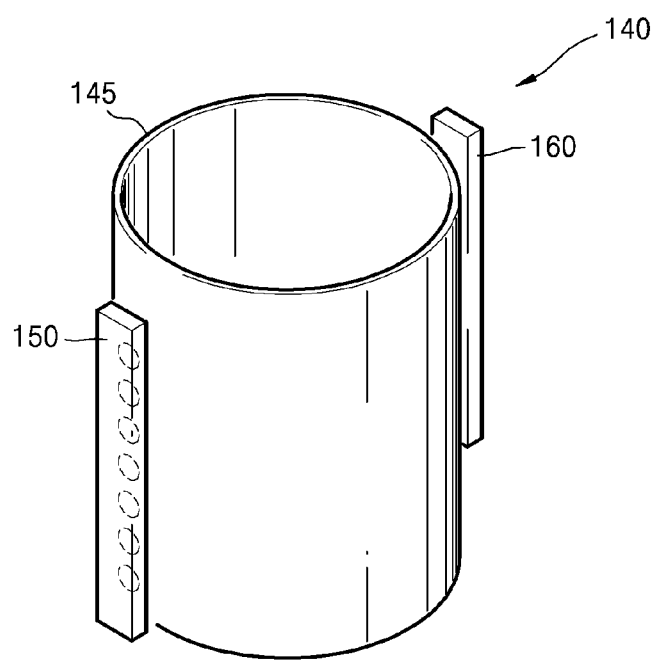
FIG. 2 is a schematic perspective view of a holder assembly employed in the X-ray imaging apparatus of FIG. 1.
Figure 3:
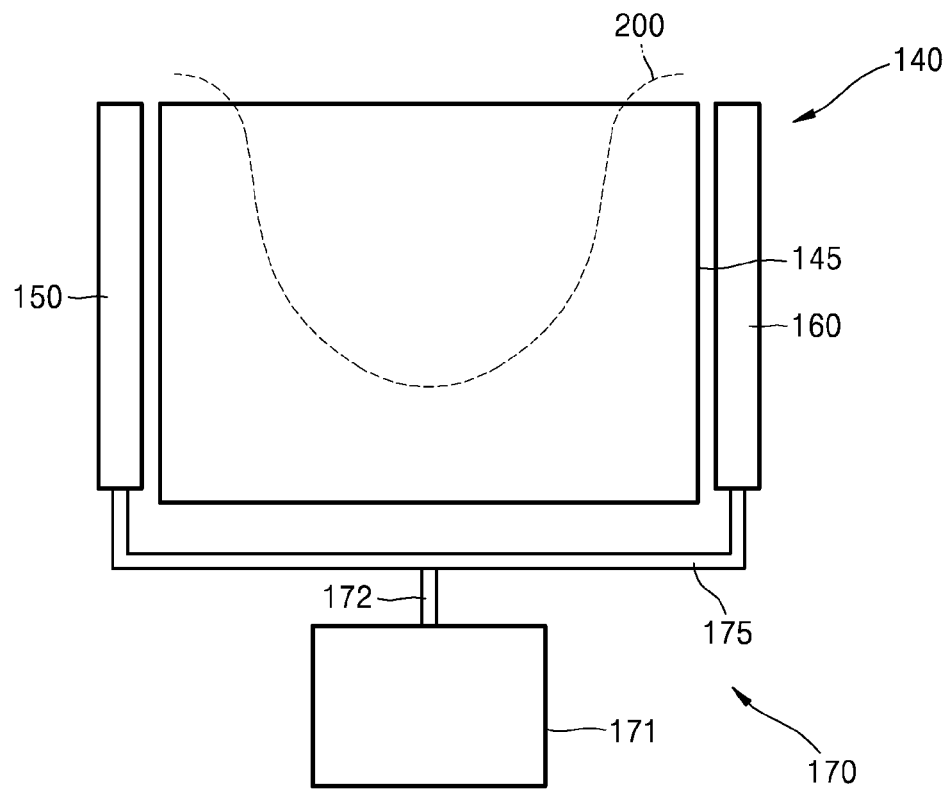
FIG. 3 is a side view of the holder assembly of FIG. 2.

FIG. 2 is a schematic perspective view of the holder assembly 140 employed in the X-ray imaging apparatus 100 of FIG. 1. FIG. 3 is a side view of the holder assembly 140 of FIG. 2. In FIG. 2, a rotation driver 170 is omitted for convenience of explanation.

Referring to FIGS. 2 and 3, the holder assembly 140 includes a holder 145, a linear X-ray generator 150 and a linear X-ray detector 160 arranged outside the holder 145, and the rotation driver 170 that rotationally drives the linear X-ray generator 150 and the linear X-ray detector 160. The holder 145 accommodates the object and may have a cylindrical shape. The holder 145 may be formed of a material, such as resin, having transmissivity to an X-ray. An end portion, that is, a top end portion, of the holder 145, which is close to the table 120, may be processed to be smooth or formed of a soft material so that use convenience may be improved.

The linear X-ray generator 150 and the linear X-ray detector 160 are separately arranged on an outer surface of the holder 145 by a distance, e.g., facing each other with the holder 145 interposed therebetween.

The linear X-ray generator 150 may detect an X-ray image with a lower radiation dose, as compared to the related art, because the linear X-ray generator 150 is located closer to the object. In an exemplary embodiment, a cold-emission cathode type X-ray source is employed as an X-ray generation unit 300 of the linear X-ray generator 150, and, thus, the linear X-ray generator 150 may be made compact to be arranged close to an outer surface of the holder 145. Accordingly, an X-ray radiation dose required on the linear X-ray generator 150 may be reduced by decreasing a distance between the linear X-ray generator 150 and the object. For example, the linear X-ray generator 150 may be arranged within about 10 cm or less, for example, only within about a few centimeters from the outer surface of the holder 145, and, thus, the greatest distance between the linear X-ray generator 150 and the object may be within about 10 cm.

Also, since the linear X-ray generator 150 and the linear X-ray detector 160 are each arranged close to the outer surface of the holder 145, an X-ray radiated by the linear X-ray generator 150 may pass through the object and may be detected in a state of having reduced scattering. Since the X-ray is prevented from being radiated to an area other than the object, an amount of overall X-ray radiation may be reduced.

The two holder assemblies 140 are arranged close to each other to match the positions of the breasts. A distance between the two holder assemblies 140 may be a factor limiting the sizes of the linear X-ray generator 150 and the linear X-ray detector 160 that rotate along the circumference of the holder 145. In an exemplary embodiment, since a cold-emission cathode type X-ray source is employed as the X-ray generation unit 300 of the linear X-ray generator 150, as described later, the linear X-ray generator 150 is made compact and thus the two holder assemblies 140 may be arranged close to each other to match the positions of the breasts.

The linear X-ray generator 150 and the linear X-ray detector 160 may be rotationally driven by the rotation driver 170 by 360° or other angle along the outer circumference of the holder 145. The rotation driver 170 includes a drive motor 171 provided under the holder 145 and a power transfer unit 175 that transfers a driving force of the drive motor 171 to the linear X-ray generator 150 and the linear X-ray detector 160. The power transfer unit 175 may have an arm structure having a center portion coupled to a rotation shaft 172 of the drive motor 171 and branching in opposite directions to support the linear X-ray generator 150 and the linear X-ray detector 160. When the rotation shaft 172 of the drive motor 171 rotates, an arm of the power transfer unit 175 rotates and thus the linear X-ray generator 150 and the linear X-ray detector 160 rotate along the outer circumference of the holder 145. Although FIG. 3 illustrates that the drive motor 171 is provided under the holder 145, an exemplary embodiment is not limited thereto. In another exemplary embodiment, an additional power transfer shaft may be provided between the rotation shaft 172 of the drive motor 171 and the arm of the power transfer unit 175, and the drive motor 171 may be arranged with a greater degree of freedom.

Although the linear X-ray generator 150 and the linear X-ray detector 160 may be rotationally driven together by one rotation driver 170, as illustrated in FIG. 3, an exemplary embodiment is not limited thereto. In another exemplary embodiment, a rotation driver may be separately provided in each of the linear X-ray generator 150 and the linear X-ray detector 160 so that the linear X-ray generator 150 and the linear X-ray detector 160 may be independently and/or selectively driven. In other words, X-ray imaging may be performed in a state in which, while any one of the linear X-ray generator 150 and the linear X-ray detector 160 is fixed, the other one is rotated. For example, while the linear X-ray generator 150 that rotates along the outer circumference of the holder 145 radiates an X-ray, the linear X-ray generator 150 in a fixed state detects the X-ray so that a set of X-ray image data is obtained. Then, the linear X-ray detector 160 is rotated by an angle and the above process of obtaining another set of X-ray image data is repeated, thereby obtaining a tomography image.

Figure 4:
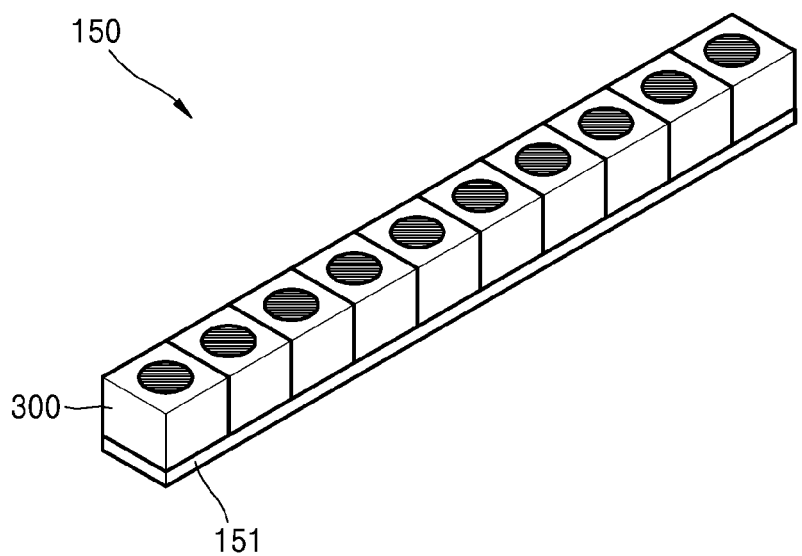
FIG. 4 illustrates an example of a linear X-ray generator employed in the holder assembly of FIG. 2.

FIG. 4 illustrates an example of the linear X-ray generator 150. As illustrated in FIG. 4, the linear X-ray generator 150 may include a plurality of the X-ray generation units 300 arranged in one dimension, i.e., as a 1D array. Each of the X-ray generation units 300 may be a cold-emission cathode type X-ray source.

Each of the X-ray generation units 300 may be independently driven to generate an X-ray. Accordingly, all of the X-ray generation units 300 may be driven to radiate an X-ray to the object or some of the X-ray generation units 300 are driven to radiate an X-ray. Also, at least two of the X-ray generation units 300 may be simultaneously or sequentially driven with one or more of other ones of the X-ray generation units. When the X-ray generation units 300 are sequentially driven or partially driven, only some X-ray detection units 1010 of FIG. 12A or 12B corresponding to the X-ray generation units 300 may be driven.

Although FIG. 4 illustrates that the X-ray generation units 300 are formed on a single substrate 151, an exemplary embodiment is not limited thereto. In another exemplary embodiment, each of the X-ray generation units 300 is separately manufactured and the X-ray generation units 300 are assembled into the linear X-ray generator 150. Alternatively, some of the X-ray generation units 300 are formed on a single substrate and then assembled together with other X-ray generation units 300 formed on other substrates. Although it is not illustrated in FIG. 4, an X-ray controller for controlling a proceeding path of an X-ray generated by each of the X-ray generation units 300 not to interfere with a neighboring X-ray may be provided. In the X-ray controller, an opening is formed in an area corresponding to each of the X-ray generation units 300 and an X-ray absorbing material may be formed in a grid type in the other area, for example, a boundary area between the neighboring X-ray generation units 300.

Figure 5A:
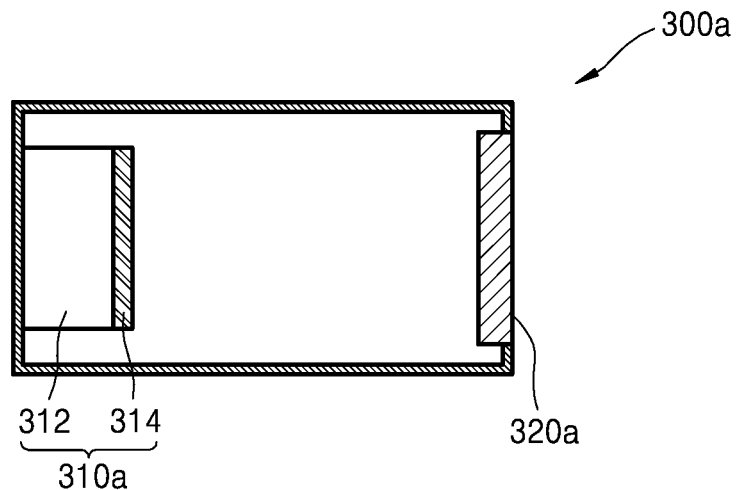
FIGS. 5A, 5B, 5C, and 5D schematically illustrate X-ray generation units according to exemplary embodiments.

FIGS. 5A to 5D schematically illustrate X-ray generation units 300a, 300b, 300c, and 300d according to exemplary embodiments. As illustrated in FIG. 5A, the X-ray generation unit 300a may include an electron emission device 310a that emits electrons and an anode electrode 320a that emits an X-ray by collision of the emitted electrons. The anode electrode 320a may include metal or a metal alloy such as W, Mo, Ag, Cr, Fe, Co, Cu, etc.

The electron emission device 310a may include a cathode electrode 312 and an electron emission source 314 arranged on the cathode electrode 312 and that emits electrons. The cathode electrode 312 may be metal such as Ti, Pt, Ru, Au, Ag, Mo, Al, W, or Cu, or a metal oxide such as indium tin oxide (ITO), aluminum zinc oxide (AZO), indium zinc oxide (IZO), tin oxide ($SnO_2$), or indium oxide ($In_2O_3$). The electron emission source 314 may be formed of a material capable of emitting electrons. For example, the electron emission source 314 may be formed of metal, silicon, an oxide, diamond, diamond like carbon (DLC), a carbide compound, a nitrogen compound, carbon nanotube, carbon nanofiber, etc. The electron emission device 310a is an example of the cold-emission cathode type X-ray source.

The cathode electrode 312 applies a voltage to the electron emission source 314. When a voltage difference occurs between the electron emission source 314 and the anode electrode 320a, that is, the cathode electrode 312 and the anode electrode 320a, the electron emission source 314 emits electrons and the electrons collide with the anode electrode 320a. Accordingly, the anode electrode 320a radiates an X-ray due to the collision of electrodes.

Figure 5B:
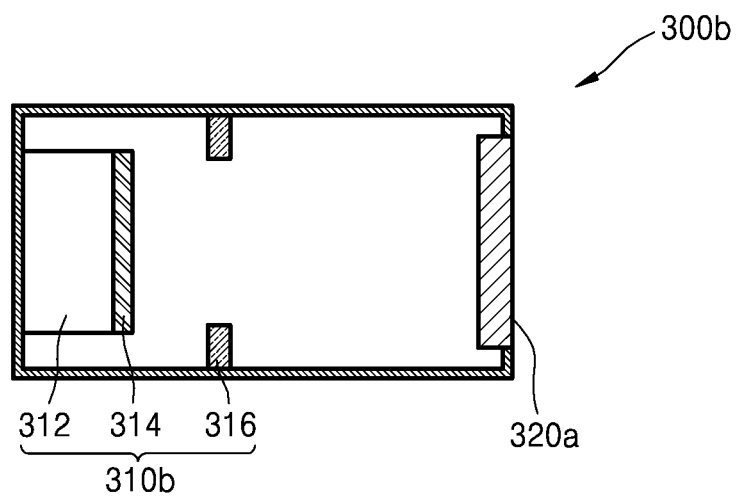

As illustrated in FIG. 5B, an electron emission device 310b of the X-ray generation unit 300b may further include a gate electrode 316 between the electron emission source 314 and the anode electrode 320a. The gate electrode 316 may be formed of the same material as the cathode electrode 312. The electron emission source 314 may emit electrons by the voltage difference between the gate electrode 316 and the cathode electrode 312. As the gate electrode 316 is arranged between the cathode electrode 312 and the anode electrode 320a, the electrons induced by the electron emission source 314 by the voltage applied to the gate electrode 316 may be controlled. Accordingly, the X-ray generation unit 300b may more stably control the emission of electrons.

Figure 5C:
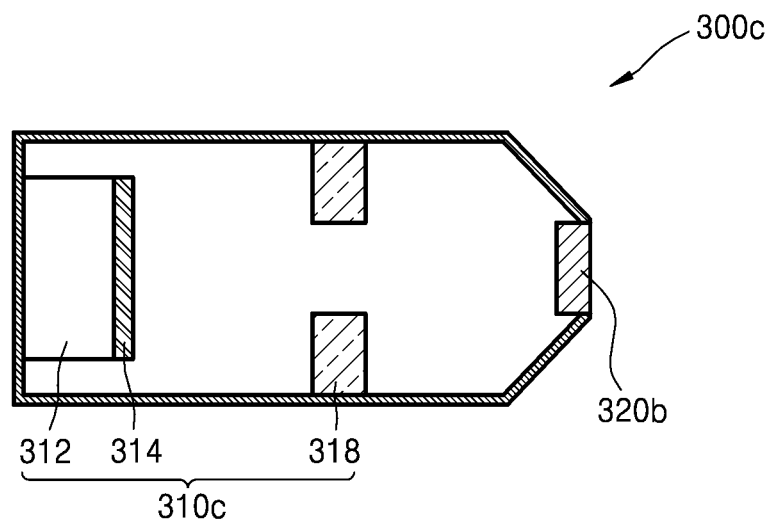

As illustrated in FIG. 5C, an electron emission device 310c of the X-ray generation unit 300c may further include a focusing electrode 318 between the electron emission source 314 and an anode electrode 320b. The focusing electrode 318 may be formed of the same material as the cathode electrode 312. The focusing electrode 318 focuses the electrons emitted from the electron emission source 314 on an area of the anode electrode 320b so as to collide therewith. The focusing electrode 318 may increase X-ray generation efficiency. A voltage applied to the focusing electrode 318 may be the same as or similar to the voltage applied to the gate electrode 316 so that an optimal focusing performance may be maintained.

Figure 5D:
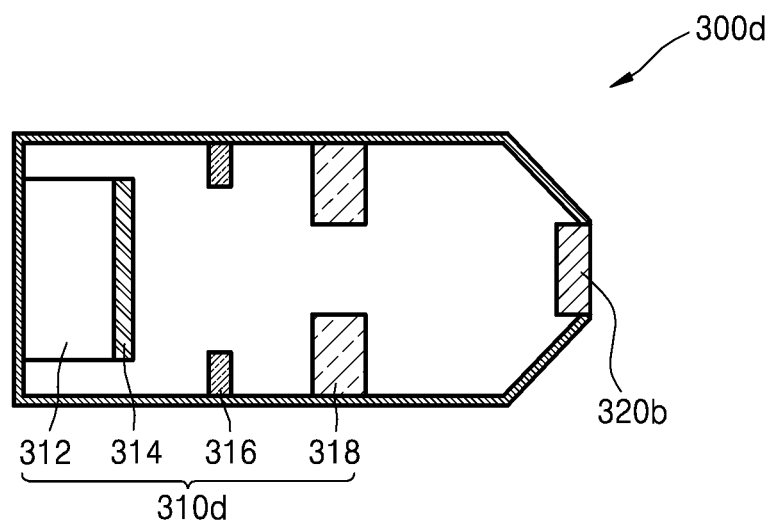

As illustrated in FIG. 5D, an electron emission device 310d of the X-ray generation unit 300d may include the cathode electrode 312, the electron emission source 314 that is arranged on the cathode electrode 312 and emits electrons, the gate electrode 316 arranged separately from the cathode electrode 312, and the focusing electrode 318 focusing the emitted electrons.

Figure 6:
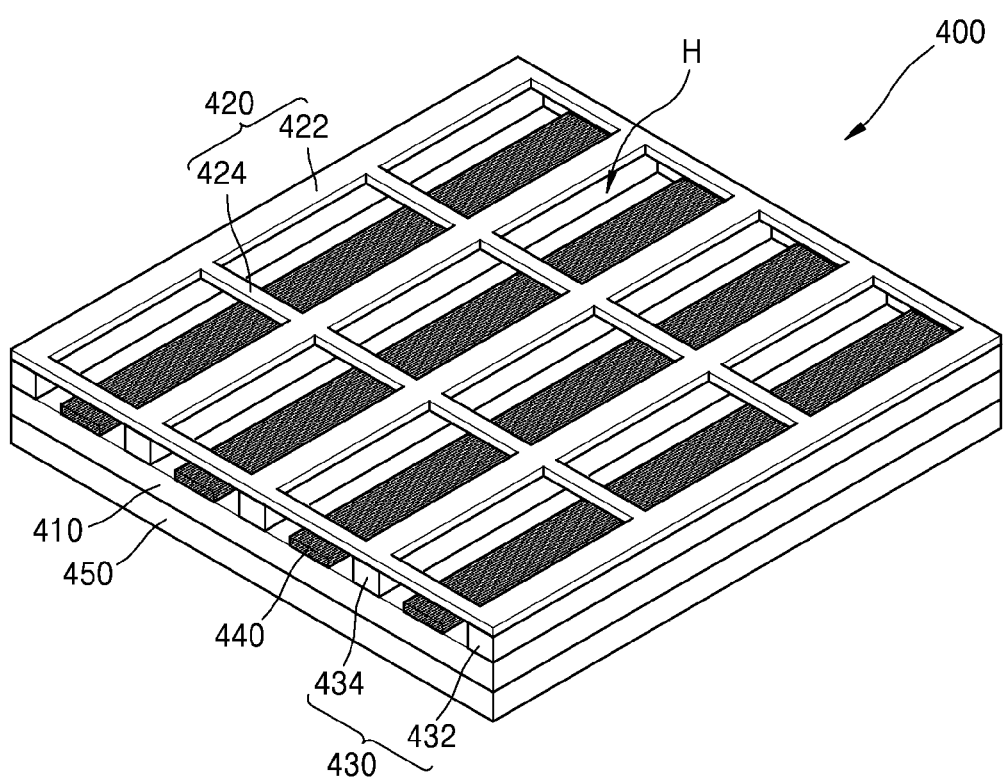
FIG. 6 illustrates an electron emission device including a gate electrode, according to an exemplary embodiment.

FIG. 6 illustrates an electron emission device 400 including a gate electrode 420, according to an exemplary embodiment. As illustrated in FIG. 6, the electron emission device 400 may include a cathode electrode 410, the gate electrode 420 having a mesh structure arranged separately from the cathode electrode 410, and a plurality of insulation layers 430 and a plurality of electron emission sources 440 extending in a first direction between the cathode electrode 410 and the gate electrode 420 and arranged separately from each other in a second direction that is perpendicular to the first direction. A substrate 450 for supporting the electron emission device 400 may be formed of an insulation material such as glass. The substrate 450 may support a single electron emission device 400 or a plurality of electron emission devices.

The cathode electrode 410 and the gate electrode 420 may be formed of a conductive material. The cathode electrode 410 may apply a voltage to each of the electron emission sources 440 and may have a flat panel shape. When the cathode electrode 410 has a flat panel shape, the substrate 450 may be omitted. The gate electrode 420 may have a mesh structure including a plurality of openings H. For example, the gate electrode 420 may include a plurality of gate lines 422 separately from each other arranged on the insulation layers 430 and a plurality of gate bridges 424 connecting the gate lines 422. Accordingly, the two neighboring gate lines 422 and the two neighboring gate bridges 424 form one opening H.

The opening H may be arranged to expose at least a part of the electron emission sources 440 between the insulation layers 430. Since the gate electrode 420 has a mesh structure, a large electron emission device 400 may be manufactured. Although FIG. 6 illustrates that the openings H of the gate electrode 420 are each rectangular, an exemplary embodiment is not limited thereto. In another embodiments, the shape of each opening H may be one of a circle, an oval, and a polygon. The sizes of the openings H may be identical or different.

The insulation layers 430 are arranged between the cathode electrode 410 and the gate electrode 420 and prevent electrical connection between the cathode electrode 410 and the gate electrode 420. Also, the insulation layers 430 are arranged in multiple numbers and at least three insulation layers 430 may be provided. The insulation layers 430 may have a linear shape. The insulation layers 430 extend in one direction and are separate from one another in another direction and support the gate electrode 420. The insulation layers 430 may each include a first insulation layer 432 supporting an edge area of the gate electrode 420 and a second insulation layer 434 supporting a middle area of the gate electrode 420.

The insulation layers 430 may be formed of an insulation material used for a semiconductor device. For example, the insulation layers 430 may be formed of at least one high-K material, as for example, hafnium oxide ($HfO_2$), aluminum oxide ($Al_2O_3$), and/or silicon nitride ($Si_3N_4$), which are high-K materials having a higher dielectric rate than, for example, silicon dioxide ($SiO_2$).

Although FIG. 6 illustrates that the insulation layers 430 have a linear shape, an exemplary embodiment is not limited thereto. The insulation layers 430 may have a different shape that prevents the electrical connection between the cathode electrode 410 and the gate electrode 420 and supports the gate electrode 420. For example, the second insulation layer 434 may have a column shape and may be arranged under the gate lines 422.

The electron emission sources 440 emit electrons by the voltage applied to the cathode electrode 410 and the gate electrode 420. The electron emission sources 440 may be alternately arranged between the insulation layers 430. For example, the electron emission sources 440 may be arranged separately from one another with the second insulation layer 434 interposed between the neighboring electron emission sources 440. The electron emission sources 440 may have a shape of strips extending in the first direction, like the second insulation layer 434.

The gate electrode 420 is arranged above the electron emission sources 440 which may be arranged separately from the gate electrode 420 to prevent the electron emission sources 440 and the gate electrode 420 from being short-circuited.

The electron emission sources 440 may be formed of a material capable of emitting electrons. As an area occupied by the electron emission sources 440 in the electron emission device 400 increases, the electron emission device 400 may emit a large amount of electrons. However, the electron emission device 400 may endure an electrostatic force due to a difference in the voltages applied between the electron emission sources 440 and the gate electrode 420. To prevent this problem, the insulation layers 430 and the electron emission sources 440 of an exemplary embodiment are alternately arranged, and the gate electrode 420 having the opening H is arranged over an area where each of the electron emission sources 440 is arranged, thereby embodying the electron emission device 400.

Since the gate electrode 420 includes the gate bridges 424 arranged in a direction crossing the lengthwise direction of the electron emission sources 440, a uniform electric field may be formed on surfaces of the electron emission sources 440.

Although FIG. 6 illustrates that the electron emission sources 440 are formed in strips, an exemplary embodiment is not limited thereto. The electron emission sources 440 may be formed as a point type in an area corresponding to the opening H above the cathode electrode 410. The point-type electron emission sources 440 may be arranged in a 2D array, that is, in a matrix format.

Also, although FIG. 6 illustrates that the electron emission sources 440 are arranged in the single electron emission device 400, an exemplary embodiment is not limited thereto. Also, only one electron emission source may be arranged in the electron emission device 400 or two or more electron emission sources may be arranged therein.

A proceeding path of the X-ray may be controlled by the shape of an anode electrode. In detail, as the thickness of the anode electrode is provided to be irregular, the proceeding path of the X-ray radiated from the anode electrode may be controlled.

FIGS. 7A, 7B, 7C, 7D, 7E, 7F, and 7G illustrate anode electrodes having irregular thicknesses according to exemplary embodiments. The anode electrode illustrated in each of FIGS. 7A to 7G corresponds to the single linear X-ray generator 150. However, an exemplary embodiment is not limited thereto. One anode electrode may correspond to one electron emission device. For convenience of explanation, one anode electrode corresponding to the single linear X-ray generator 150 will be described below.

Figure 7A:
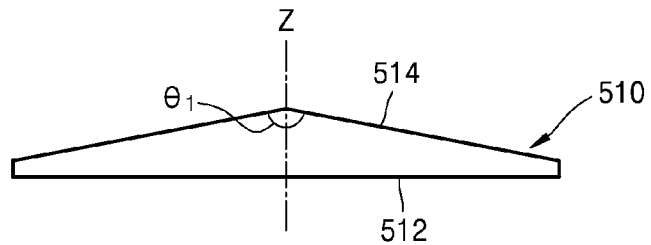
FIGS. 7A, 7B, 7C, 7D, 7E, 7F, and 7G illustrate anode electrodes having irregular thicknesses, according to exemplary embodiments.
Figure 7B:
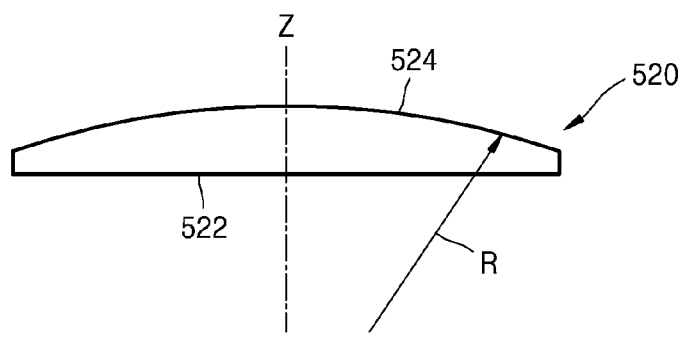

As illustrated in FIGS. 7A to 7G, the anode electrode may be symmetrically provided about a center axis Z of each linear X-ray generator 150 so that an X-ray may be symmetrically radiated. The thicknesses of anode electrodes 510 and 520 gradually decrease from the center axis Z of the linear X-ray generator 150 toward edges thereof, as illustrated in FIGS. 7A and 7B, and X-rays radiated from the anode electrodes 510 and 520 may progress to be focused at the center axis Z of the linear X-ray generator 150. The linear X-ray generator 150 may efficiently radiate an X-ray in a partial area of the object.

In detail, surfaces 512 and 522 of the anode electrodes 510 and 520, on which electrons are incident, may be flat surfaces, whereas surfaces 514 and 524 from which X-rays exit may be protruding surfaces with respect to the flat surfaces 512 and 522. The surfaces 514 and 524 from which X-rays exit may be convexly curved surfaces or convex surfaces obtained by combining flat surfaces. A position where the X-ray is focused may be determined by an angle θ1 and a radius R of the corresponding convex structures. Although in FIGS. 7A and 7B the surfaces 512 and 522 of the anode electrodes 510 and 520 on which electrons are incident are flat and the surfaces 514 and 524 from which X-rays exit are protruding, an exemplary embodiment is not limited thereto. That is, the surfaces on which electrons are incident may be convex, whereas the surfaces from which X-rays exit may be flat.

Figure 7C:
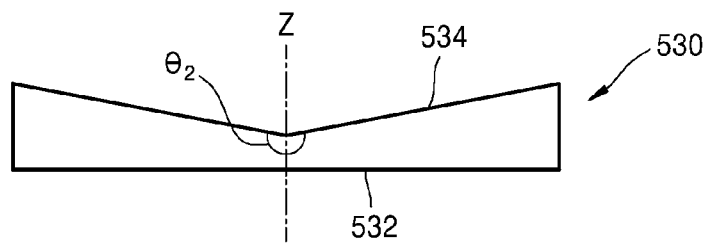
Figure 7D:
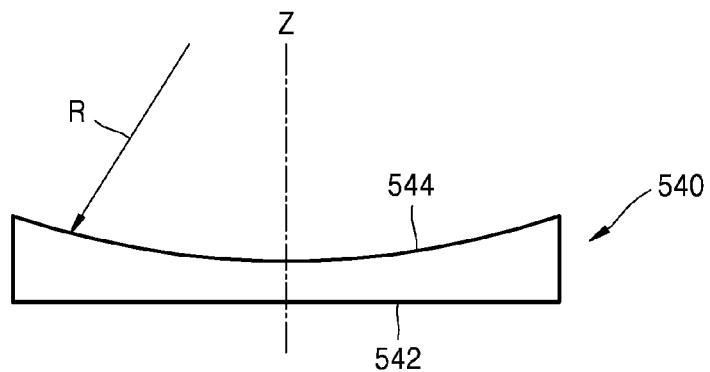

Thicknesses of anode electrodes 530 and 540 gradually increase from the center axis Z of the linear X-ray generator 150 toward edges thereof, as illustrated in FIGS. 7C and 7D and the X-ray radiated from each of the anode electrodes 530 and 540 may progress toward an area larger than an X-ray emitting area of each of the anode electrodes 530 and 540. Accordingly, the linear X-ray generator 150 may radiate an X-ray to an object having a relatively large area.

In detail, surfaces 532 and 542 of the anode electrode 530 and 540, on which electrons are incident, may be flat surfaces, whereas surfaces 534 and 544 from which X-rays exit may be concave surfaces with respect to flat surfaces 532 and 542. The surfaces 534 and 544 from which X-rays exit may be concavely curved surfaces or concave surfaces obtained by combining flat surfaces. A size of an area where the X-ray is radiated may be determined by an angle θ2 and a radius R of corresponding concave structures. Although in FIGS. 7C and 7D the surfaces 532 and 542 of the anode electrodes 530 and 540 on which electrons are incident are flat and the surfaces 534 and 544 from which X-rays exit are concave, an exemplary embodiment is not limited thereto. That is, the surfaces on which electrons are incident may be concave, whereas the surfaces from which X-rays exit may be flat.

Figure 7E:
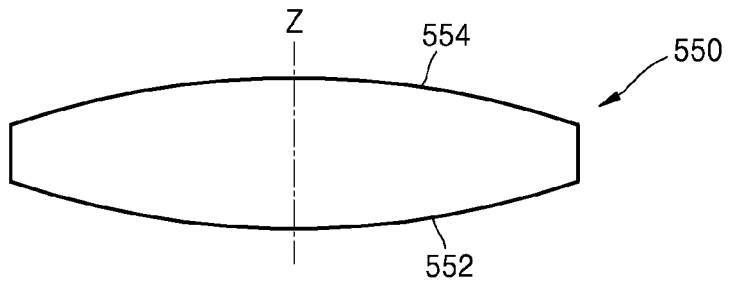

As illustrated in FIG. 7E, both surfaces 552, 554 of an anode electrode 550 on which electrons are incident and from which X-rays exit may be convex with respect to one another. In this case, a focal distance of an X-ray may become shorter. As another example, both surfaces on which electrons are incident and from which X-rays exit may be concave with respect to one another. Alternatively, while one of the surfaces on which electrons are incident and from which X-rays exit may be concave, the other surface may be convex.

Figure 7F:
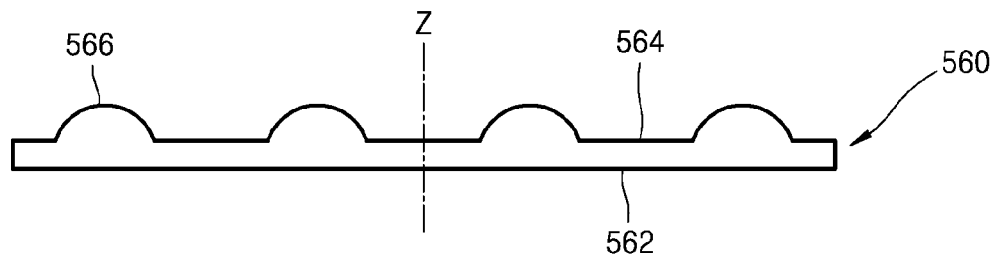
Figure 7G:
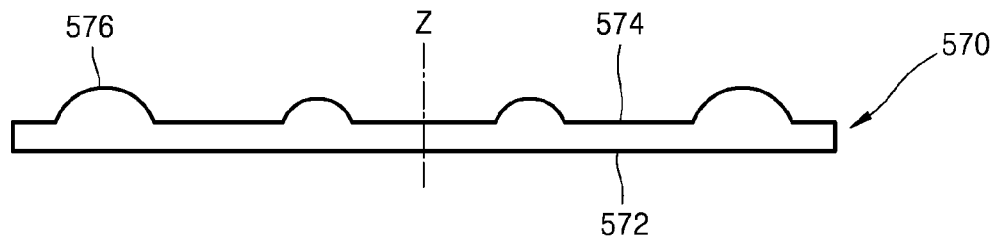

The thickness of an anode electrode may be partially irregular. For example, as it is illustrated in FIGS. 7F and 7G, anode electrodes 560 and 570 may have a shape in which only some portions are convex with respect to bottom flat surfaces 562, 572. A convex structure 566 may be identical to other convex structures or a convex structure 576 may be different from other convex structures according to an area. The thicknesses of the convex structures 576 may be symmetrical with respect to the center axis Z of the linear X-ray generator 150. Although FIGS. 7F and 7G illustrate only a convex structure, an exemplary embodiment is not limited thereto. The anode electrode may include a concave structure or both a concave structure and a convex structure.

As such, since the progress path of an X-ray may be controlled by using the anode electrode having an irregular thickness, the linear X-ray generator 150 may efficiently radiate an X-ray to the object and may also reduce an X-ray radiation dose.

Figure 8:
FIG. 8 illustrates an anode electrode having a uniform thickness, according to an exemplary embodiment.

The X-ray imaging apparatus according to an exemplary embodiment may use an anode electrode having a uniform thickness. FIG. 8 illustrates an anode electrode 580 having a uniform thickness, according to an exemplary embodiment. Referring to FIG. 8, while the anode electrode 580 having a uniform thickness is used, the progress path of an X-ray may be controlled by using a separate element such as a collimator (not shown).

Figure 9A:
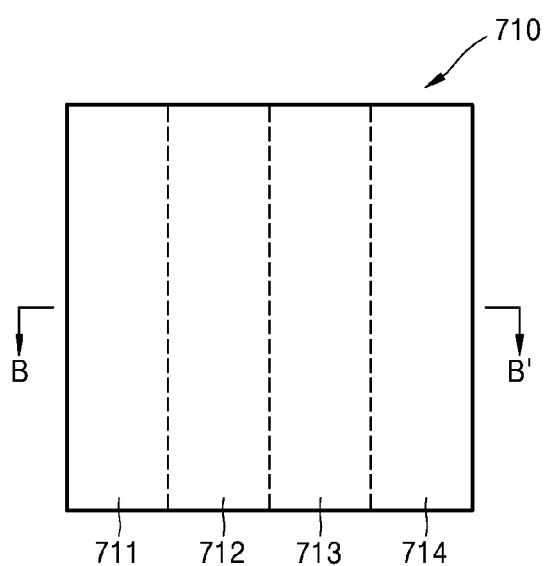
FIGS. 9A and 9B illustrate an anode electrode formed of different materials, according to an exemplary embodiment.
Figure 9B:
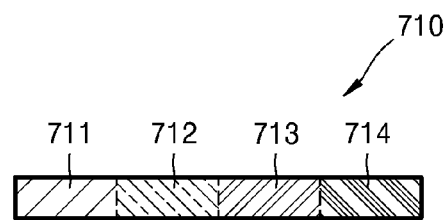

The anode electrode may include a plurality of layers formed of different materials and capable of radiating X-rays of different wavelengths. FIGS. 9A and 9B illustrate an anode electrode 710 formed of different materials, according to an exemplary embodiment. As it is illustrated in FIG. 9, the anode electrode 710 may include a plurality of layers 711, 712, 713, and 714 formed of different materials. The layers 711, 712, 713, and 714 may be parallelly arranged with respect to an electron emission device. The anode electrode 710 may radiate X-rays of different wavelengths according to the layers 711, 712, 713, and 714 with which electrons collide.

An anode electrode radiating X-rays of multiple wavelengths may have a non-uniform thickness as described above. FIGS. 10A, 10B, 10C, and 10D illustrate anode electrodes 810 and 820 formed of different materials, according to exemplary embodiments. Each of the anode electrodes 810 and 820 may include a plurality of layers formed of different materials and at least one of the layers may have an irregular thickness.

Figure 10A:
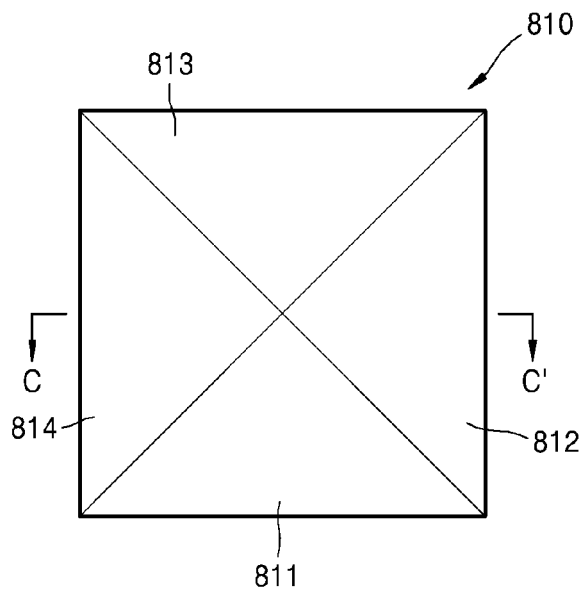
FIGS. 10A, 10B, 10C, and 10D illustrate anode electrodes formed of different materials, according to exemplary embodiments.
Figure 10B:
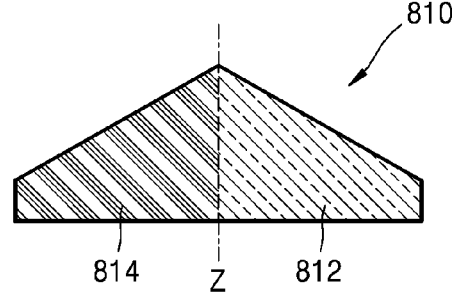

For example, as illustrated in FIGS. 10A and 10B, the anode electrode 810 may include a plurality of layers 811, 812, 813, and 814 that are formed of different materials. The layers 811, 812, 813, and 814 have thicknesses that gradually decrease from the center axis Z of the linear X-ray generator 150 toward edges thereof. Accordingly, the anode electrode 810 may focus the radiated X-rays. Since the X-rays having different wavelengths are focused on different areas, a single linear X-ray generator may image many different areas having different depths of the object at one time.

Figure 10C:
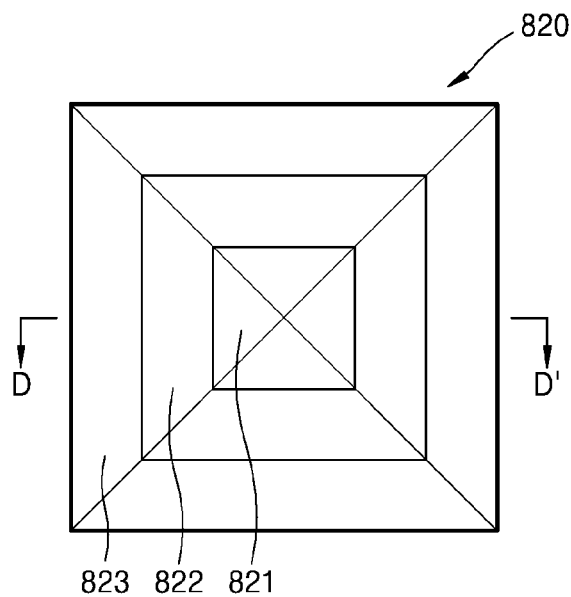
Figure 10D:
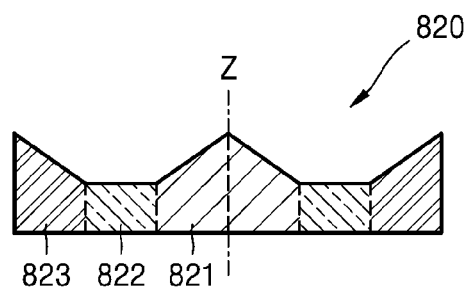

As illustrated in FIGS. 10C and 10D, the anode electrode 820 may include a plurality of layers 821, 822, and 823 that are formed of different materials. The anode electrode 820 may have a change in the thickness thereof according to the layers 821, 822, and 823. For example, the first layer 821 may have a thickness that gradually decreases from the center axis Z of the linear X-ray generator 150 toward an edge thereof, the second layer 822 may have a uniform thickness, and the third layer 823 may have a thickness that gradually increases with respect to the center axis Z of the linear X-ray generator 150 toward the edge thereof. Accordingly, the anode electrode 820 may radiate an X-ray to a larger surrounding area while focusing on an area of interest of the object.

Figure 11A:
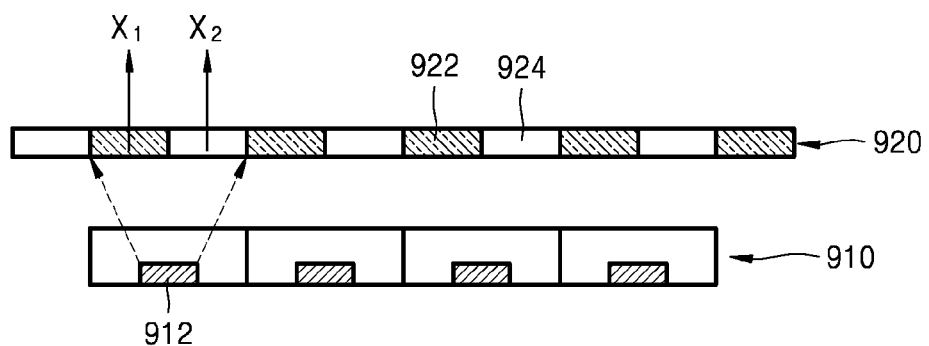
FIGS. 11A, 11B, and 11C illustrate an X-ray generator generating an X-ray of a short wavelength or an X-ray of a plurality of wavelength bands according to exemplary embodiments.
Figure 11B:
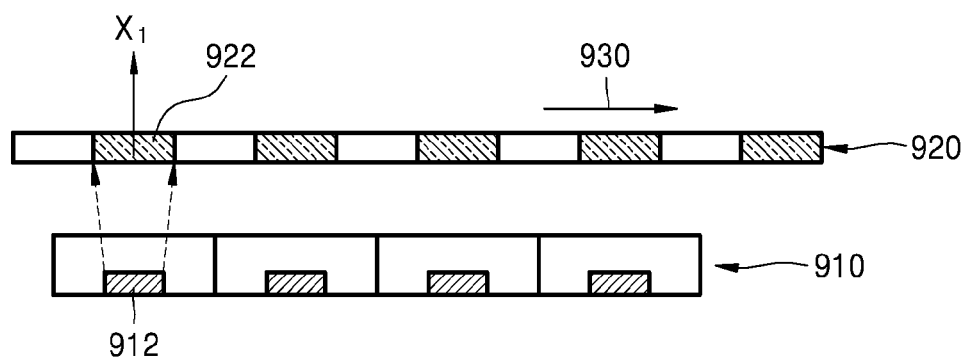
Figure 11C:
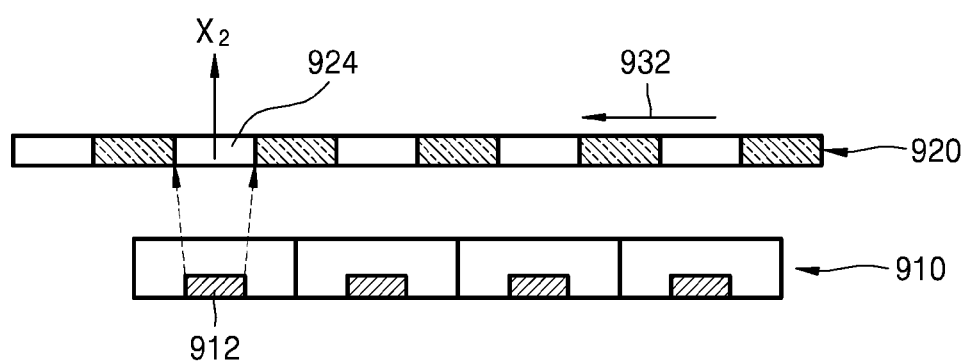

Also, the linear X-ray generator 150 according to an exemplary embodiment may simultaneously or selectively generate X-rays of different wavelengths. FIGS. 11A to 11C illustrate an X-ray generator generating an X-ray of a short wavelength or simultaneously generating X-rays of a plurality of wavelength bands, according to exemplary embodiments.

Referring to FIG. 11A, a plurality of electron emission devices 910, each having an electron emission source 912, and an anode electrode 920 may be arranged separately from one another. In the anode electrode 920, first and second layers 922 and 924 that are formed of different materials may be alternately arranged. When the first and second layers 922 and 924 overlap with each other in an area corresponding to the electron emission source 912 of one of the electron emission devices 910, electrons emitted by the electron emission devices 910 may collide with the first and second layers 922 and 924. Accordingly, the anode electrode 920 may simultaneously radiate a first X-ray X1 and a second X-ray X2.

As illustrated in FIGS. 11B and 11C, the anode electrode 920 makes a translational movement in parallel with the electron emission devices 910 in one of a direction 930 and a direction 932. In FIG. 11B, the anode electrode 920 makes a translational movement in parallel with the electron emission devices 910 such that the first layer 922 of the anode electrode 920 may be arranged to overlap or align with the electron emission source 912. The electrons emitted by the electron emission devices 910 collide with the first layer 922 and thus the first X-ray X1 of a first wavelength may be radiated from the anode electrode 920.

As illustrated in FIG. 11C, the anode electrode 920 makes a translational movement in parallel with the electron emission devices 910 such that the second layer 924 of the anode electrode 920 may be arranged to overlap or align with the electron emission source 912. The electrons emitted by the electron emission devices 910 collide with the second layer 924 and thus the second X-ray X2 of a second wavelength may be radiated from the anode electrode 920.

As such, since the anode electrode 920 simultaneously radiates a plurality of X-rays or selectively radiates a single X-ray, usability of the linear X-ray generator 150 may be improved.

As described above, the X-ray generation units 300 are arranged in the linear X-ray generator 150. Each of the X-ray generation units 300 is separately manufactured as one unit and then the X-ray generation units 300 are assembled, thereby forming the linear X-ray generator 150. Also, a plurality of electron emission devices and an anode electrode may be integrally manufactured on a single substrate. Alternatively, a plurality of electron emission devices are manufactured on a single substrate and then an anode electrode is assembled, thereby forming a linear X-ray generator. In addition, the linear X-ray generator 150 may be formed by a variety of methods.

The linear X-ray generator 150 may further include a collimator (not shown) for controlling a proceeding direction of an X-ray. Accordingly, an X-ray radiation dose may be reduced and also an X-ray may be more accurately detected.

Figure 12A:
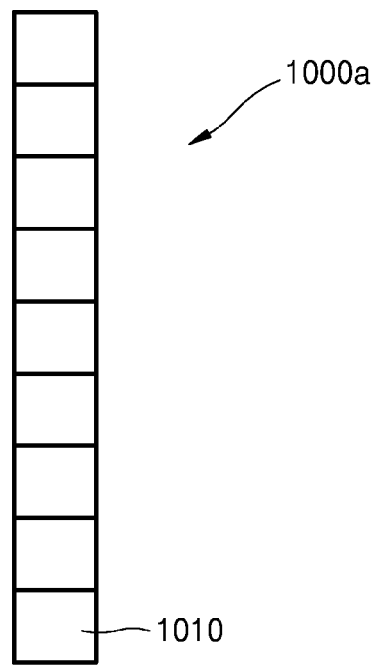
FIGS. 12A and 12B schematically illustrate X-ray detectors that may be applied to the X-ray detector of FIG. 1.
Figure 12B:
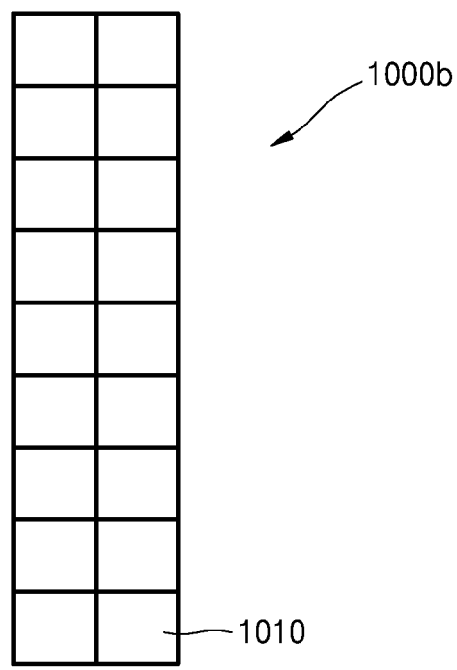

FIGS. 12A and 12B schematically illustrate linear X-ray detectors 1000a and 1000b that may be used as the X-ray detector 160 of FIG. 1. As illustrated in FIG. 12A, the linear X-ray detector 1000a may be a linear detector having a linear detection surface in which a plurality of X-ray detection units 1010 are arranged in one dimension. Alternatively, as illustrated in FIG. 12B, the linear X-ray detector 1000b may be a linear detector having a linear detection surface in which the one-dimensional arrangement of the X-ray detection units 1010 is provided in two or more rows.

Figure 13A:
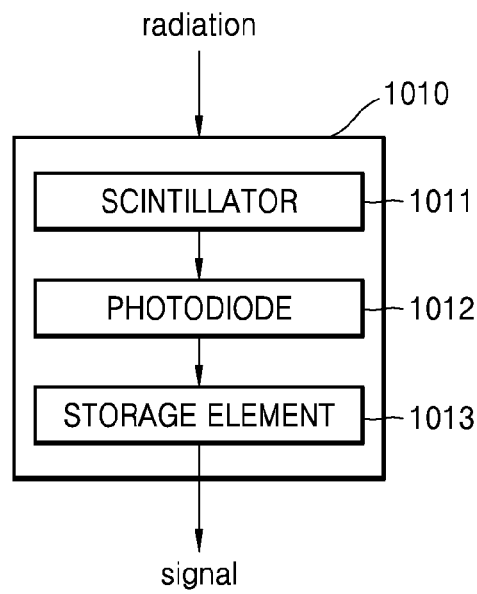
FIGS. 13A and 13B schematically illustrate examples of an X-ray detection unit that may be applied to the X-ray detector of FIG. 1.

Each of the X-ray detection units 1010 is a light-receiving element that receives an X-ray and converts a received X-ray into an electric signal. For example, as illustrated in FIG. 13A, each of the X-ray detection units 1010 may be an indirect type X-ray receiving element including a scintillator 1011, a photodiode 1012, and a storage element 1013. The scintillator 1011 receives an X-ray and outputs photons, in particular visible photons, that is, a visible ray, according to a received X-ray. The photodiode 1012 receives the photons output from the scintillator 1011 and converts received photons into electric signals. The storage element 1013 is electrically connected to the photodiode 1012 and stores the electric signal output from the photodiode 1012. The storage element 1013 may be, for example, a storage capacitor. The electric signal stored in the storage element 1013 of each of the X-ray detection units 1010 is applied to a signal processor (not shown) where the signal is processed into an X-ray image.

Figure 13B:
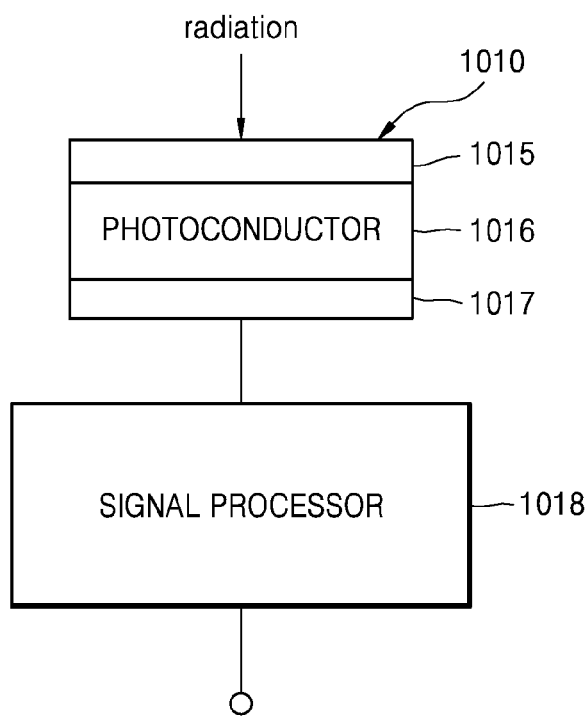

In another example, as illustrated in FIG. 13B, each of the X-ray detection units 1010 may be a direct type X-ray receiving element including a photoconductor 1016 converting an X-ray into an electric signal, electrodes 1015 and 1017 respectively formed on upper and lower portions of the photoconductor 1016, and a signal processor 1018 counting the electric signals transmitted from the electrode 1017 in the lower portion.

The X-ray detection units 1010 may be provided to correspond to the X-ray generation units 300 of the linear X-ray generator 150, respectively. The X-ray generation units 300 and the X-ray detection units 1010 may have a one-to-one correspondence. Each of the X-ray generation units 300 may correspond to two or more X-ray detection units 1010, or two or more X-ray generation units 300 may correspond to one X-ray detection unit 1010.

The X-ray detection units 1010 may be simultaneously or independently driven to detect an X-ray. Accordingly, an X-ray irradiated onto the entire area of the object may be detected as all of the X-ray detection units 1010 are driven, or an X-ray irradiated onto a particular area of the object may be detected as some of the X-ray detection units 1010 are driven. Also, at least two of the X-ray detection units 1010 may be simultaneously or sequentially driven.

Figure 14:
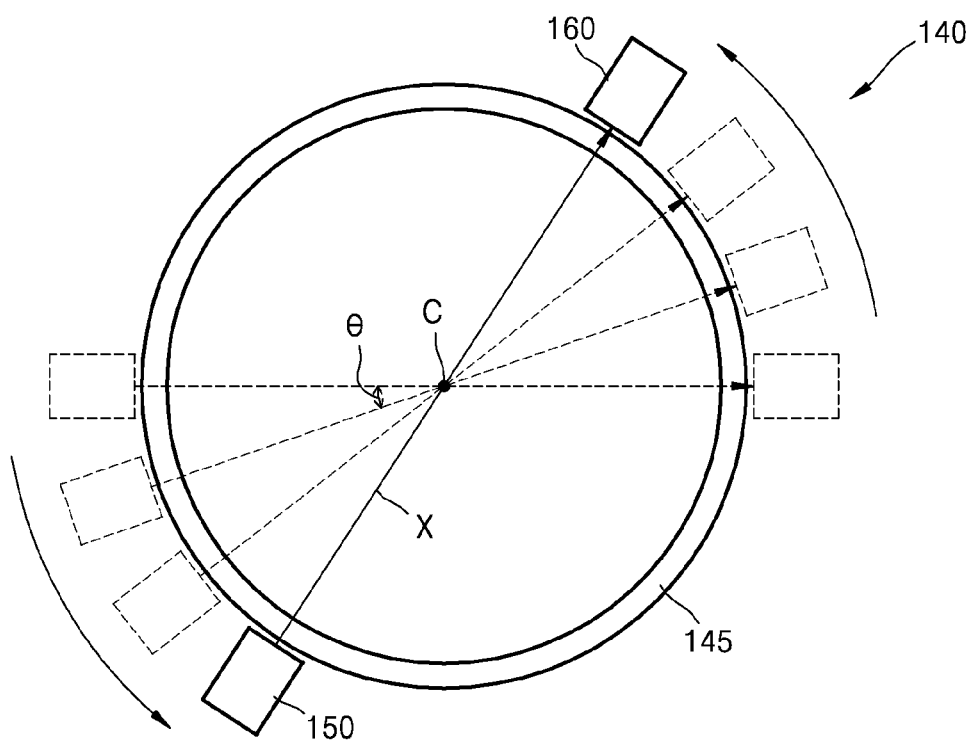
FIG. 14 illustrates an operation of the holder assembly of FIG. 2.

Also, the X-ray detection units 1010 may be integrally formed on a signal substrate or separately manufactured and then assembled into the linear X-ray detector 160. Next, the operation of the holder assembly 140 according to an exemplary embodiment will be described below with reference to FIG. 14.

The linear X-ray generator 150 provided at one side of the holder 145 radiates an X-ray having a long linear beam sectional shape toward a center portion C of the holder 145. The linear X-ray detector 160 provided at the other side with respect to the holder 145 detects the X-ray passing through the center portion C of the holder 145. Since the object is provided in the holder 145, an X-ray signal detected by the linear X-ray detector 160 includes image information of the object.

When the linear X-ray generator 150 and the linear X-ray detector 160 perform X-ray imaging by rotating by 360° along the outer circumference of the holder 145, tomographic information of the object is obtained for rotational angles θ of the linear X-ray generators 150 and 160 and thus tomography may be obtained based on the obtained tomographic information and angular information. Tomographic images may be reconstructed in two or three dimensions based on the obtained tomographic information and angular information. Also, a tomosynthesis image may be obtained. Since an image processing algorithm to obtain a tomographic image or a tomosynthesis image from the tomographic information and the angular information is known to those skilled in the art, a detailed description thereof will be omitted.

Figure 15:
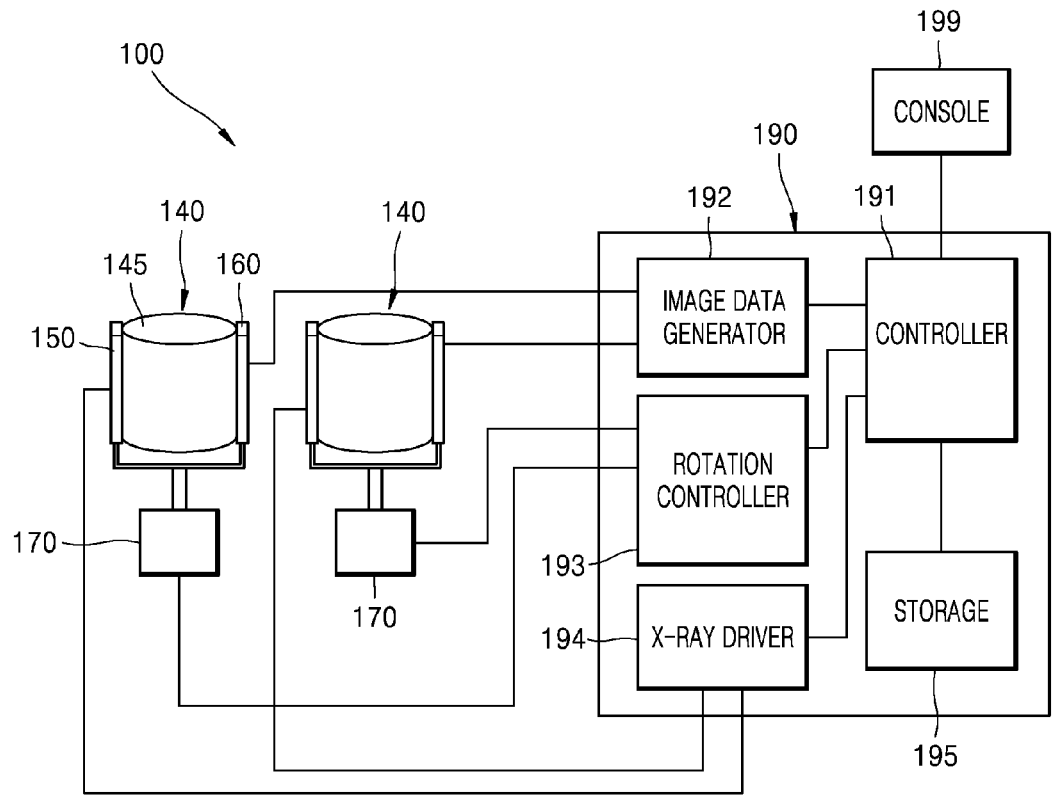
FIG. 15 is a block diagram of the X-ray imaging apparatus of FIG. 1.

FIG. 15 is a block diagram of the X-ray imaging apparatus 100 of FIG. 1. Referring to FIG. 15, the X-ray imaging apparatus 100 according to an exemplary embodiment includes the holder assembly 140 and the control apparatus 190 controlling the holder assembly 140. As described above, the holder assembly 140 includes the holder 145, the linear X-ray generator 150, the linear X-ray detector 160, and the rotation driver 170 that rotationally drives the linear X-ray generator 150 and the linear X-ray detector 160.

The control apparatus 190 may include a controller 191, an image data generator 192, a rotation controller 193, an X-ray driver 194, and a storage 195. The control apparatus 190 may receive an input of a command of X-ray imaging from a user. Information about a command to drive the linear X-ray generator 150 and the linear X-ray detector 160 of the holder assembly 140, a command to rotationally drive the linear X-ray generator 150 of the holder assembly 140, a command to control a parameter to change a spectrum of an X-ray, etc., which are input by a user, may be transferred to the controller 191. The controller 191 controls the elements in the control apparatus 190 according to the user's command.

The image data generator 192 receives electric signals corresponding to the X-ray detected by the linear X-ray detector 160 of the holder assembly 140. The image data generator 192 generates digital section data containing information about a section of the object, from the received electric signals, i.e., the section data. One-time radiation of an X-ray generates one section data containing information about a section of the object. When an X-ray is radiated many times by changing the position of the linear X-ray generator 150, a plurality of pieces of section data about different sections of the object may be generated. When any pieces of neighboring section data of the generated section data are accumulated, 3D volume data representing the object in three dimensions may be generated.

The rotation controller 193 controls the rotation driving of the linear X-ray generator 150 and the linear X-ray detector 160. The X-ray driver 194 controls the X-ray generation units 300 of the linear X-ray generator 150 in FIG. 4. Also, the X-ray driver 194 may control X-ray radiation intensity of the X-ray generation units 300. For example, the X-ray driver 194 may control rotation and activation of each of the X-ray generation units 300 individually or may control rotation and activation of any number of the X-ray generation units 300 together, e.g., in groups. Also, the X-ray driver 194 may control X-ray radiation intensity of each of the X-ray generation units 300 individually or may control radiation intensities of any number of the X-ray generation units 300 together, e.g., in groups.

The storage 195 may store the section data and/or the 3D volume data generated by the image data generator 192. The storage 195 may transmit to the console 199 the stored section data or 3D volume data on a user's request.

Figure 16:
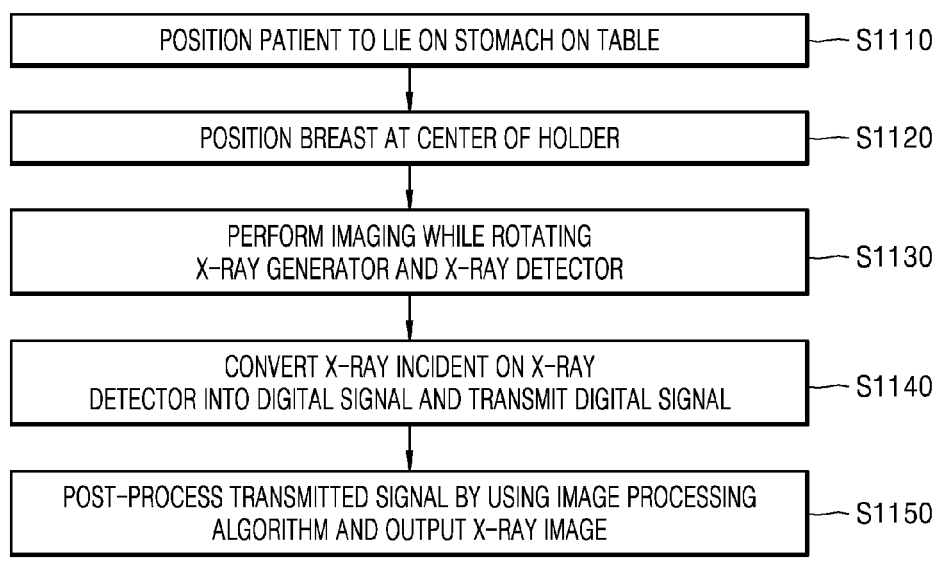
FIG. 16 is a flowchart of a method of operating an X-ray imaging apparatus, according to an exemplary embodiment.

FIG. 16 is a flowchart of a method of operating the X-ray imaging apparatus 100, according to an exemplary embodiment. Referring to FIG. 16, a patient lies on her stomach on the table 120 of FIG. 1 (operation S1110). Next, the object, that is, the breast of the patient, is fixedly disposed at the center portion C of the holder 145 (operation S1120). Next, X-ray imaging is performed by driving the holder assembly 140 (operation S1130). In other words, the linear X-ray generator 150 and the linear X-ray detector 160 are rotated by driving the rotation driver 170 and then the X-ray radiation of the linear X-ray generator 150 and the X-ray detection of the linear X-ray detector 160 are activated. The X-ray radiation of the linear X-ray generator 150 and the X-ray detection of the linear X-ray detector 160 may be continuously or discontinuously performed. The rotation ranges of the linear X-ray generator 150 and the linear X-ray detector 160 may vary according to the purpose of imaging, for example, obtaining tomographic images or tomosynthesis images. During the X-ray imaging, an X-ray signal input to the linear X-ray detector 160 is converted into a digital signal and then transmitted to the image data generator 192 of FIG. 15 (operation S1140). The image data generator 192 post-processes the transmitted signal by using an image processing algorithm and outputs an X-ray image (operation S1150).

Since the X-ray imaging apparatus 100 according to an exemplary embodiment performs X-ray imaging when the object (the breast of a patient) is placed in the holder 145, there is no need to press the object. In the related art mammography apparatus, X-ray imaging is performed when the breast is pressed and thus a patient feels discomfort. In contrast, the breast is not pressed during the X-ray imaging by the X-ray imaging apparatus 100 according to an exemplary embodiment.

Further, in the X-ray imaging apparatus 100 according to an exemplary embodiment, the imaging of a left mediolateral oblique (LMLO) view, a right mediolateral oblique (RMLO) view, a left craniocaudal (LCC) view, and a right craniocaudal (RCC) view may be completed as the linear X-ray generator 150 and the linear X-ray detector 160 rotate once so that a workflow may be reduced and the X-ray radiation dose to a patient may be reduced. Furthermore, since the X-ray imaging apparatus 100 according to an exemplary embodiment simultaneously images both breasts of a patient by using the two holder assemblies 140, the workflow may be further reduced.

Although in an exemplary embodiment a patent lies on her stomach on the table 120, an exemplary embodiment is not limited thereto. It is possible that the table 120 stands vertically and thus imaging is performed while a patient stands. In this case, the table 120 may be a support for supporting and guiding a patient.

Also, although in an exemplary embodiment the holder assembly 140 is arranged in both through-holes 125, the holder assembly 140 may be arranged in any one of the two through-holes 125.

The X-ray imaging apparatus 100 may image the entire object or a partial area of the object in one operation. For example, when an X-ray generation area of the linear X-ray generator 150 and an X-ray detection area of the linear X-ray detector 160 are equal to or larger than a test area of the object, the linear X-ray generator 150 and the linear X-ray detector 160 may image the object by one operation. When a partial area of the object is to be imaged, only some of the X-ray generation units 300 of the linear X-ray generator 150 are operated to generate an X-ray and only some of the X-ray detection units 1010 of the linear X-ray detector 160 corresponding to the operating X-ray generation units 300 may detect the X-ray.

When the an X-ray generation area of the linear X-ray generator 150 and an X-ray detection area of the linear X-ray detector 160 are smaller than the test area of the object, at least one of the linear X-ray generator 150 and the linear X-ray detector 160 may be driven two times or more.

Figure 17:
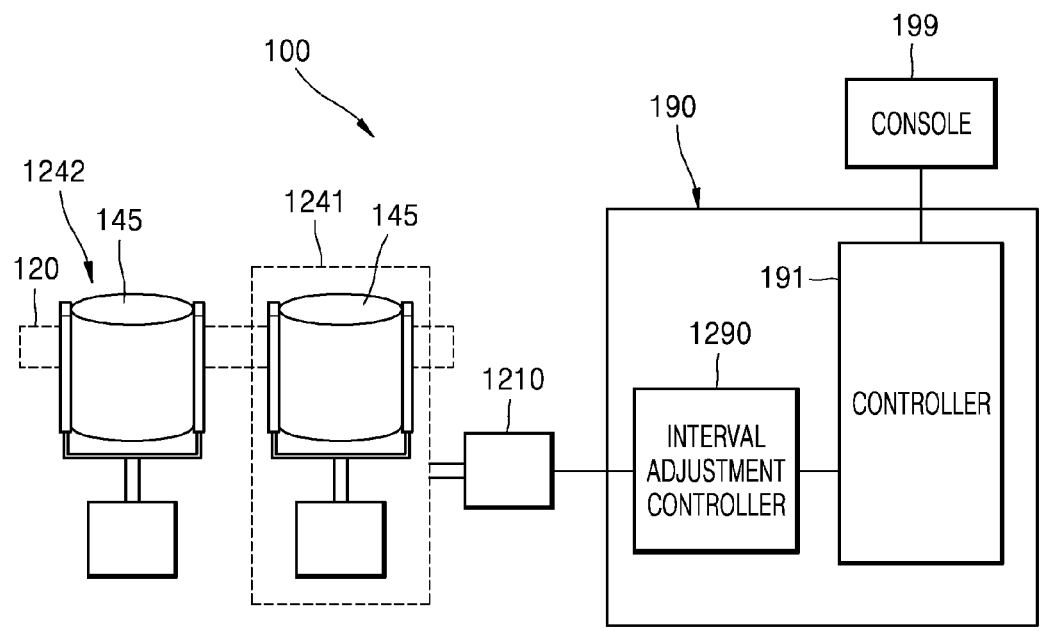
FIG. 17 is a schematic block diagram of an X-ray imaging apparatus according to an exemplary embodiment.

FIG. 17 is a schematic block diagram of an X-ray imaging apparatus 100 according to an exemplary embodiment. The X-ray imaging apparatus 100 according to an exemplary embodiment may include an interval adjuster 1210 for adjusting a distance between the two holder assemblies 140.

Referring to FIG. 17, the X-ray imaging apparatus 100 includes a movable holder assembly 1241 and a fixed holder assembly 1242. The movable holder assembly 1241 and the fixed holder assembly 1242 are each substantially the same as the holder assembly 140 of the X-ray imaging apparatus 100 described with reference to FIGS. 1 to 16. While the movable holder assembly 1241 is movably provided on the table 120 of FIG. 1, the fixed holder assembly 1242 is fixed on the table 120. The interval adjuster 1210 may automatically move the movable holder assembly 1241 by using a driver such as an electrostatic motor, a hydraulic device, etc. The control apparatus 190 may further include an interval adjustment controller 1290 to control driving of the interval adjuster 1210.

Although in an exemplary embodiment the entire movable holder assembly 1241 is moved by the interval adjuster 1210, an exemplary embodiment is not limited thereto. In another exemplary embodiment, the interval adjuster 1210 may be coupled only to the holder 145 of the movable holder assembly 1241 to move the holder 145 only. Alternatively, a power transfer shaft may be additionally provided between the rotation shaft 172 of the drive motor 171 and the power transfer unit 175 so that, while the drive motor 171 may be fixed, the other elements of the movable holder assembly 1241 may be moved by the internal adjuster 1210.

Figure 18:
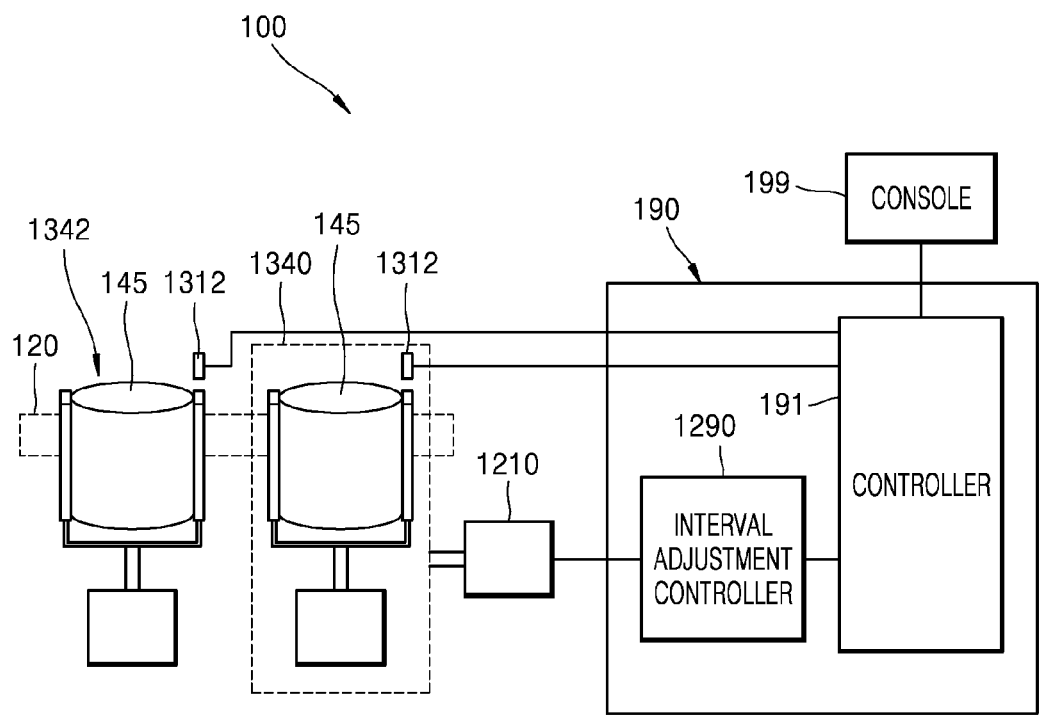
FIG. 18 is a schematic block diagram of an X-ray imaging apparatus according to an exemplary embodiment.
Figure 19:
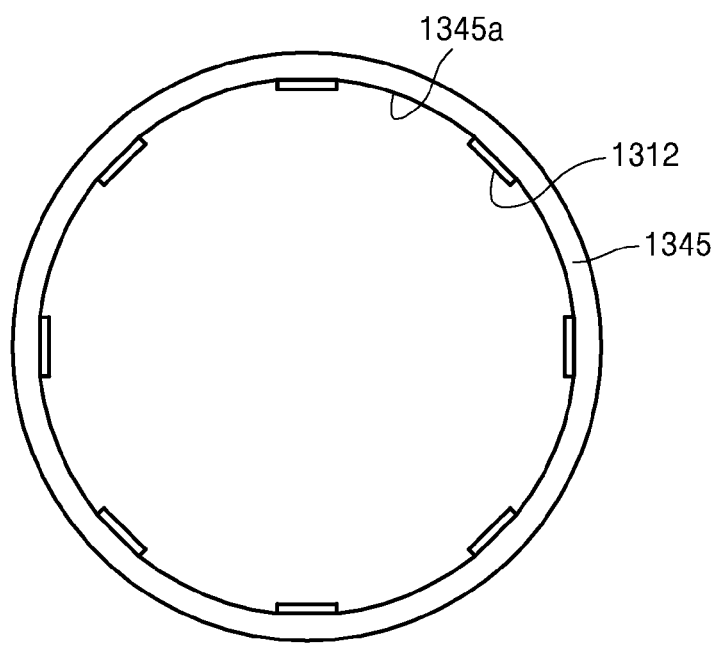
FIG. 19 illustrates an example of an arrangement of contact sensors that are provided on a cylindrical holder assembly of the X-ray imaging apparatus of FIG. 18.

FIG. 18 is a schematic block diagram of an X-ray imaging apparatus 100 according to an exemplary embodiment. FIG. 19 illustrates an example of an arrangement of contact sensors 1312 that are provided on a cylindrical holder assembly 1340, 1342 of the X-ray imaging apparatus 100 of FIG. 18.

Referring to FIGS. 18 and 19, the contact sensors 1312 are arranged at a constant interval in alignment with or on an inner circumferential surface 1345*a* of a holder 1345. Furthermore, the contact sensors 1312 may be arranged in the vicinity of an entrance of the holder 1345 and at a constant interval on the inner circumferential surface 1345*a* of the holder 1345. The contact sensors 1312 detect contact of the object and are used to detect whether the object is disposed at correct positions in the holder 1345. The contact sensors 1312 may be contact pressure sensors detecting a contact pressure of the object. The contact pressure sensor may be, for example, a sensor using a piezoelectric element having an electromotive force that varies according to a contact pressure, a thin film sensor having resistance that varies according to a contact pressure, or a sensor using a micro-electromechanical systems (MEMS) structure.

When the object is inserted in the holder 1345 for X-ray imaging, the contact sensor 1312 detects contact of the inserted object. When all contact sensors 1312 detect the contact of the object, the object is determined to be placed at a correct position and the X-ray imaging may be performed. When some of the contact sensors 1312 do not detect the contact of the object, the object may be regarded to be eccentrically inserted to one side. Accordingly, the holder assembly 1340 is manually or automatically moved until all contact sensors 1312 detect the contact of the object.

When the contact sensors 1312 are contact pressure sensors, the contact sensors 1312 may detect an even contact pressure of the object. In this case, the object is determined to be disposed at a correct position only when all contact pressures of the object detected by the contact sensors 1312 are within an allowable range, and then X-ray imaging may be performed. When the contact pressures of the object detected by some of the contact sensors 1312 are smaller than or larger than the allowable range, the object is regarded to be eccentrically inserted and accordingly, the holder assembly 1340 is manually or automatically moved until the contact pressures detected by all contact sensors 1312 are within the allowable range.

Although in an exemplary embodiment the contact sensors 1312 are provided on both holder assemblies 1340, 1342, the contact sensors 1312 may be provided only on the movable holder assembly 1340. Also, although in an exemplary embodiment the interval adjuster 1210 is provided, the movable holder assembly 1340 may be manually moved without using the interval adjuster 1210.

Figure 20:
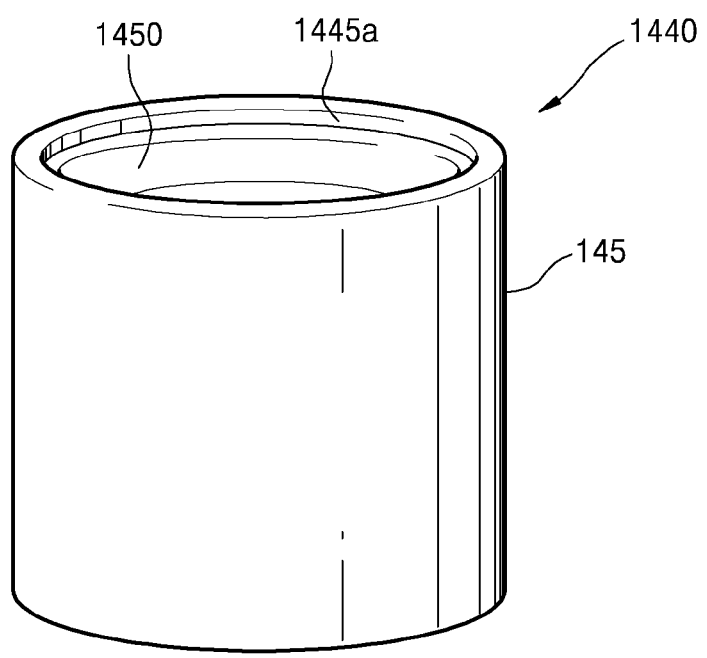
FIG. 20 illustrates a holder assembly according to an exemplary embodiment.
Figure 21:
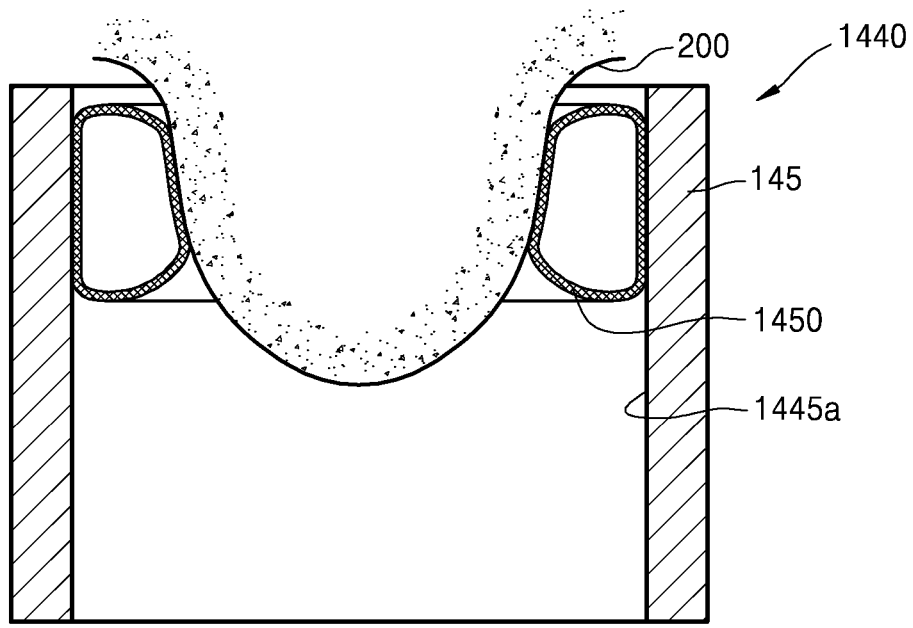
FIG. 21 illustrates an operation of the holder assembly of FIG. 20.

FIG. 20 illustrates a holder assembly 1440 according to an exemplary embodiment. FIG. 21 illustrates an operation of the holder assembly 1440 of FIG. 20. An X-ray imaging apparatus according to an exemplary embodiment may be understood as one obtained by adding a breast fixing apparatus 1450 to the X-ray imaging apparatus 100 described above.

Referring to FIGS. 20 and 21, the breast fixing apparatus 1450 may be an expandable air tube provided on an inner circumferential surface 1445*a* of a holder 145. The breast fixing apparatus 1450 may be provided in the vicinity of an entrance of the holder 145. When an object 200 is inserted in the holder 145 for X-ray imaging, the air is supplied by an air pump (not shown) to the inside of the breast fixing apparatus 1450 and the breast fixing apparatus 1450 expands to occupy the space between the object 200 and the inner circumferential surface 1445*a* as illustrated in FIG. 21, thereby fixing the object 200.

Figure 22:
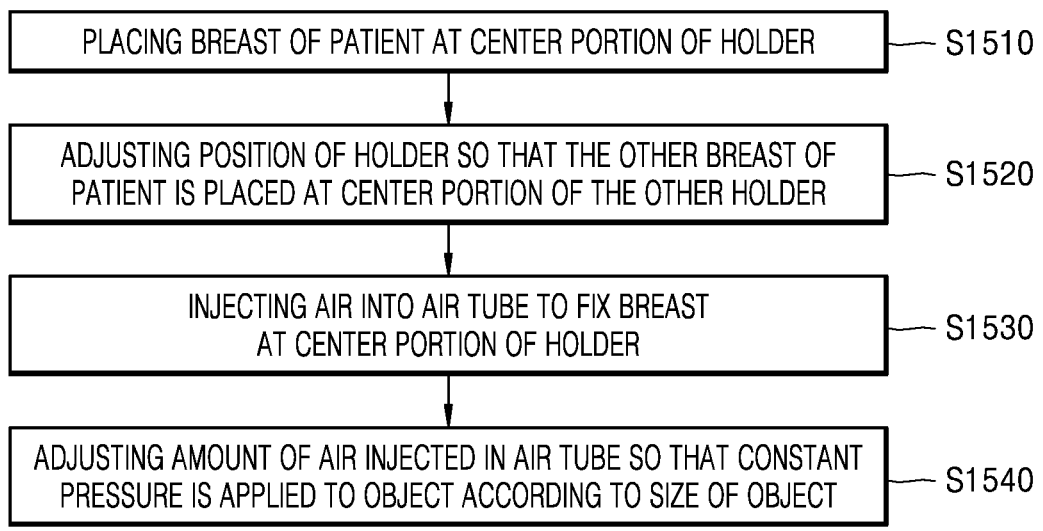
FIG. 22 is a flowchart of a method of operating an X-ray imaging apparatus employing the holder assembly of FIG. 20.

FIG. 22 is a flowchart of a method of operating an X-ray imaging apparatus according to an exemplary embodiment. Referring to FIG. 22, a method of fixing an object, according to an exemplary embodiment, includes placing one breast of a patient at a center portion of the holder 145 corresponding to the breast (operation S1510), adjusting a distance of the holder assembly 1440 such that the other breast of the patient may be disposed at a center portion of the other holder 145 (operation S1520), fixing the breast by injecting air into an air tube that is the breast fixing apparatus 1450 (operation S1530), and adjusting air in the breast fixing apparatus 1450 so that a constant pressure may be applied to the object according to the size of the object (operation S1540). The above-described breast fixing process may be additionally added between placing the object in the holder 145 (operation S1120) and performing X-ray imaging (operation S1130), which are described above with reference to FIG. 16.

Figure 23:
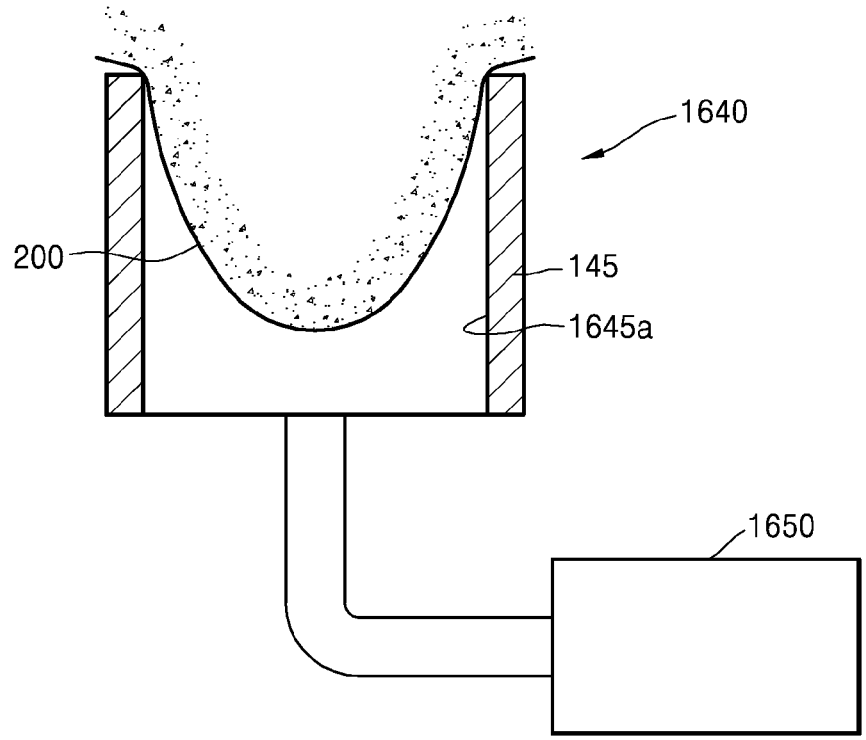
FIG. 23 illustrates a holder assembly according to an exemplary embodiment.

Although in the above description an expandable air tube is used as the breast fixing apparatus 1450, an exemplary embodiment is not limited thereto. FIG. 23 illustrates a holder assembly 1640 according to an exemplary embodiment. Referring to FIG. 23, a breast fixing apparatus 1650 may be a vacuum pump connected to a lower end of a holder 145. When the object is inserted in the holder 145 for X-ray imaging, the breast fixing apparatus 1650 softly sucks air from an inside area 1645*a* of the holder 145 so that the object is pulled and fixed.

Figure 24:
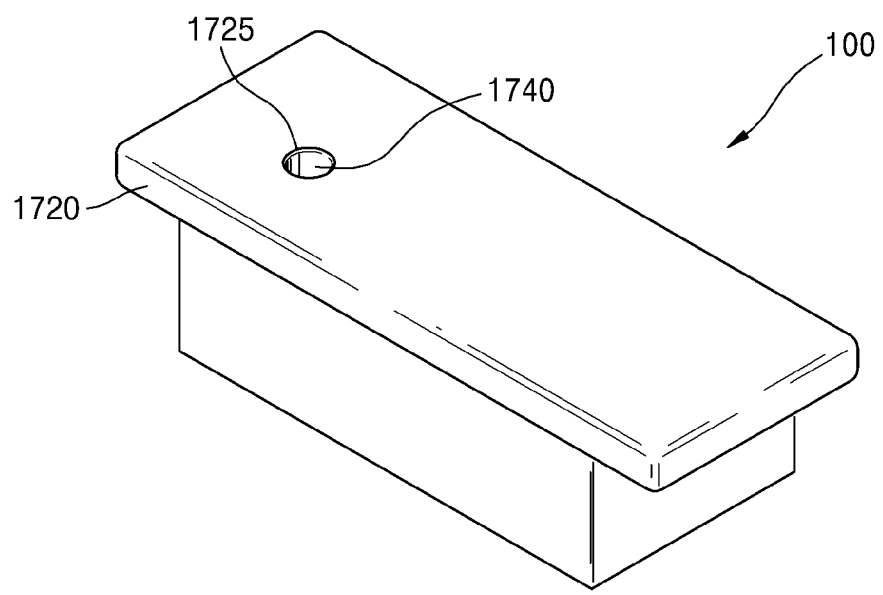
FIG. 24 is a schematic perspective view of an X-ray imaging apparatus according to an exemplary embodiment.

Although in the above-described exemplary embodiments two holder assemblies are provided, an exemplary embodiment is not limited thereto. As illustrated in FIG. 24, in an X-ray imaging apparatus 100 according to an exemplary embodiment, only one through-hole 1725 may be provided in a table 1720 and only one holder assembly 1740 may be provided in the table 1720.

Figure 25:
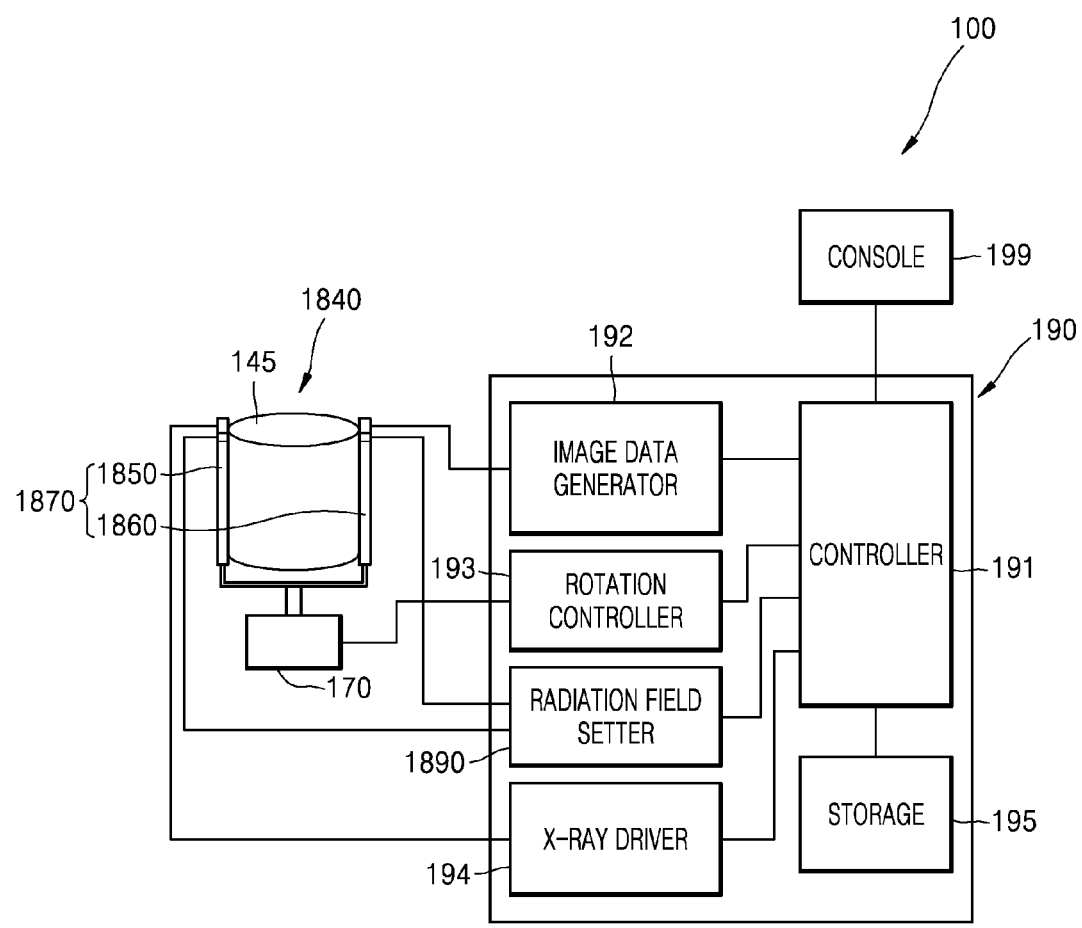
FIG. 25 is a schematic block diagram of an X-ray imaging apparatus according to an exemplary embodiment.
Figure 26:
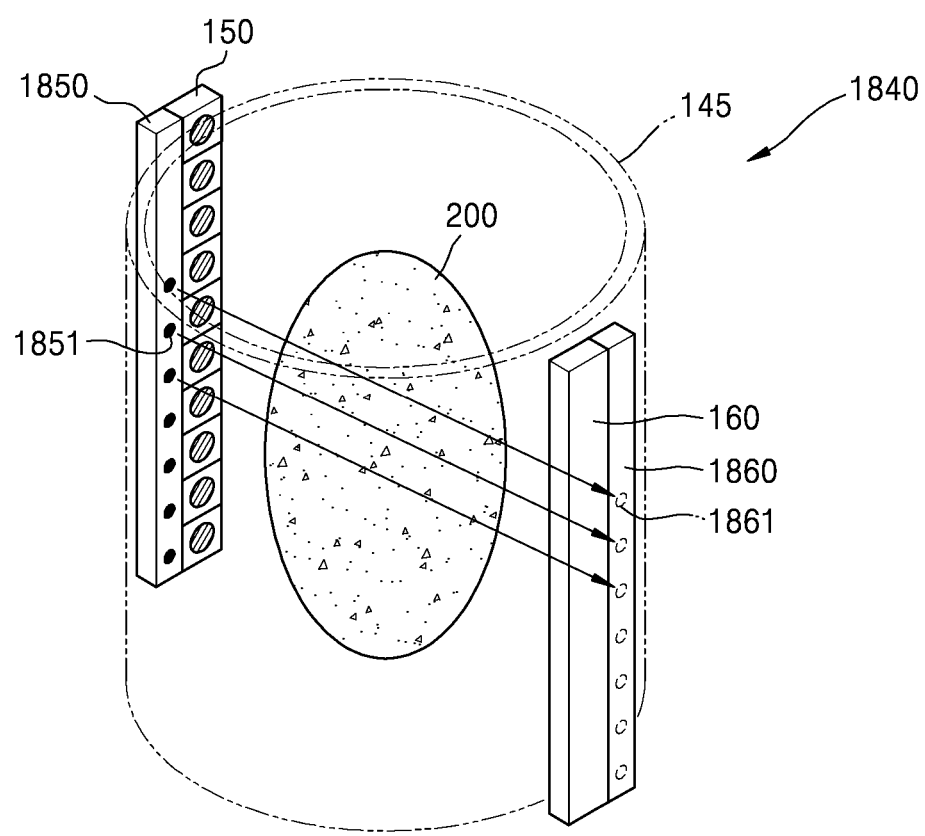
FIG. 26 illustrates a radiation field detector that is provided on a holder assembly of the X-ray imaging apparatus of FIG. 25.

FIG. 25 is a schematic block diagram of an X-ray imaging apparatus 100, according to an exemplary embodiment, which includes the holder assembly 1840 provided with the radiation field detector 1870. Although FIG. 25 illustrates a case in which only one holder assembly 1840 is provided, two holder assemblies 1840 may be provided. FIG. 26 illustrates in detail a radiation field detector 1870 of the X-ray imaging apparatus 100 of FIG. 25.

Referring to FIG. 25, the radiation field detector 1870 includes a light-emitting unit 1850, a light-receiving unit 1860, and a radiation field setter 1890 that controls the light-emitting unit 1850 and the light-receiving unit 1860 and sets a radiation field. As illustrated in FIG. 26, the light-emitting unit 1850 and the light-receiving unit 1860 may be arranged close to the linear X-ray generator 150 and the linear X-ray detector 160, respectively.

As illustrated in FIG. 26, the light-emitting unit 1850 has a structure in which a plurality of light-emitting elements 1851 are linearly arranged at an identical interval at one side of the linear X-ray generator 150. The light-emitting elements 1851 may be, for example, light-emitting diodes, organic light-emitting diodes, laser diodes, lamps, etc., which emit visible rays or infrared rays. Light emitted from the light-emitting elements 1851 may have a linear beam section that is lengthy discontinuously in the same direction as a direction in which the linear X-ray generation units 150 are arranged. In another exemplary embodiment, the light-emitting unit 1850 may have a linear light source which elongates in a direction, thus emitting light having a linear beam section that is lengthy continuously in the same direction as the direction in which the linear X-ray generation units 150 are arranged. A focusing lens such as a collimator lens may be additionally provided at a light-emitting surface of each of the light-emitting elements 1851 to allow the light rays emitted by the light-emitting elements 1851 to have a directivity. The wavelength range of the light emitted by the light-emitting elements 1851 or the type of light source is not limited.

Figure 28:
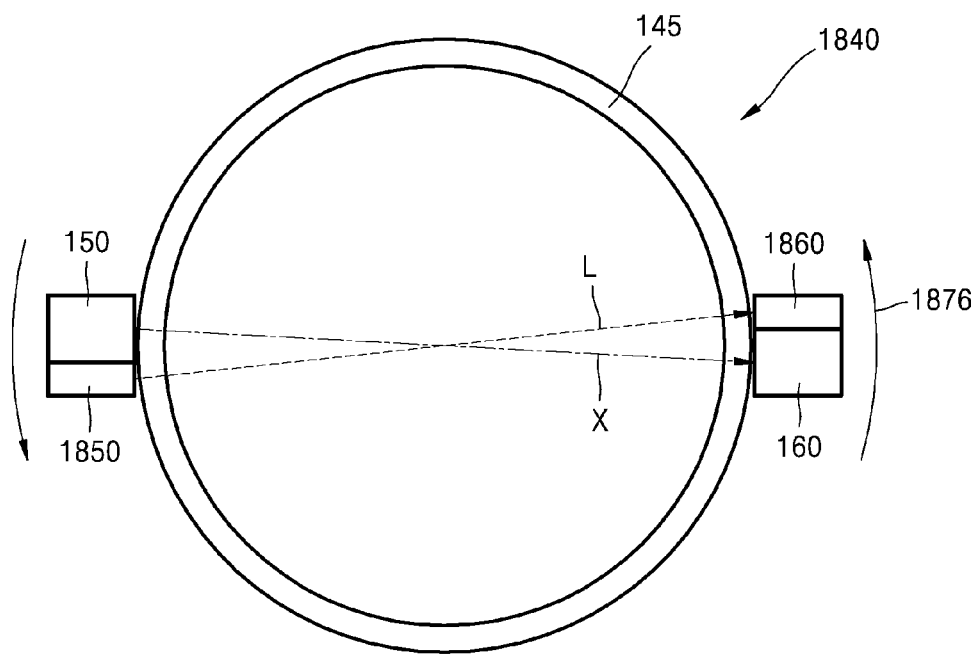
FIG. 28 illustrates an operation of the radiation field detector of FIG. 25.

The light-receiving unit 1860 has a structure in which a plurality of light-receiving elements 1861 are linearly arranged at an identical interval in a vertical direction at one side of the linear X-ray detector 160. The light-receiving elements 1861 may be photodiodes, phototransistors, or image sensors which have a detection range corresponding to the wavelength range of the light emitted by the light-emitting elements 1851. The light-emitting unit 1850 and the light-receiving unit 1860 may be respectively attached on the lateral surfaces of the linear X-ray generator 150 and the linear X-ray detector 160 at the upstream side with respect to a rotation direction 1876, as illustrated in FIG. 28. That is, the light-emitting unit 1850 and the light-receiving unit 1860 may be respectively attached on the leading surfaces of the linear X-ray generator 150 and the linear X-ray detector 160 in a rotation direction. In this case, the light emitted by the light-emitting unit 1850 proceeds toward the light-receiving unit 1860 after passing through a center portion of a holder 145. The arrangements of the light-emitting unit 1850 and the light-receiving unit 1860 are not limited thereto and thus the light-emitting unit 1850 and the light-receiving unit 1860 may be attached on the lateral surfaces of the linear X-ray generator 150 and the linear X-ray detector 160 at the downstream side with respect to the rotation direction, or vice versa.

Figure 27:
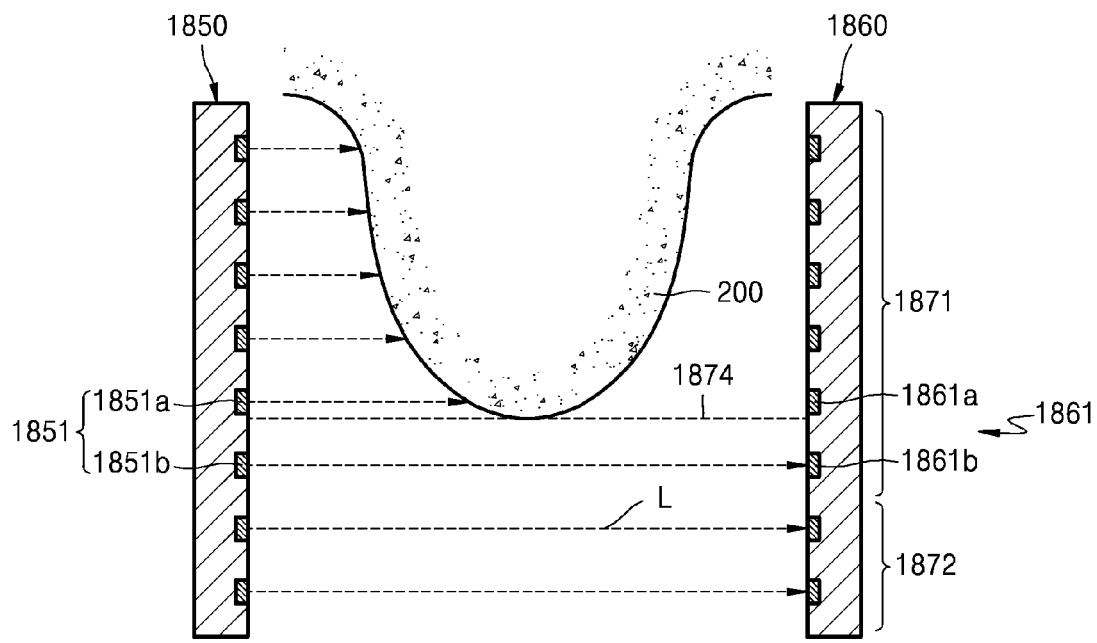
FIG. 27 illustrates an operation of the radiation field detector of FIG. 25.

FIGS. 27 and 28 illustrate an operation of the radiation field detector 1870 of FIG. 25. For convenience of explanation, the holder 145 is omitted in FIG. 27.

Referring to FIGS. 27 and 28, when the object 200 is inserted in the holder 145 for X-ray imaging, the light-emitting unit 1850 emits light L toward the light-receiving unit 1860 disposed opposite to the light-emitting unit 1850. The emitted light L proceeds toward the light-receiving unit 1860. Since the object 200 occupies a portion of an inner space of the holder 145, part of the light L does not arrive at the light-receiving unit 1860. Accordingly, there is an imaginary boundary 1874 between a light-receiving element 1861*a* that does not receive the light L and a light-receiving element 1861*b* that adjoins the light-receiving element 1861*a* and detects the light L among the light-receiving elements 1861 that are vertically arranged. In other words, the light-receiving elements 1861 may be divided into an area that does not receive the light L and an area that receives the light L according to whether the light-receiving elements 1861 receive light or not. An optical path between the light-receiving element 1861*a* that is the last one of the light-receiving elements 1861 that are vertically arranged and does not receive light, and a light-emitting element 1851*a* corresponding to the light-receiving element 1861*a* may be understood as an area where an end portion of the object 200 is located. The area 1871 that does not receive the light L may be set to be an X-ray radiation field 1871. Further, considering movements of a patient during imaging, an area including a light-receiving element 1861*b* that detects the light L and is also disposed closest to the boundary is set to be included into an X-ray radiation field 1871. Accordingly, only the X-ray generation units 300 of the linear X-ray generator 150 corresponding to the set X-ray radiation field 1871 may be activated. The outer area 1872 is a non-irradiation field where an X-ray is not irradiated.

Figure 29:
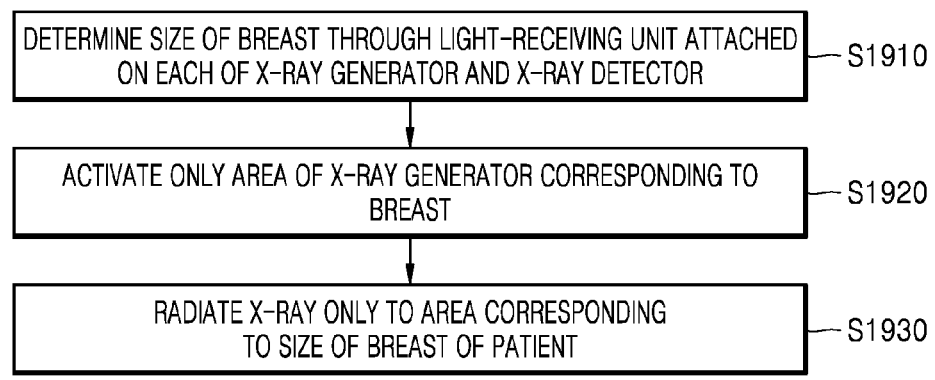
FIG. 29 is a flowchart of an operation of the X-ray imaging apparatus of FIG. 24.

FIG. 29 is a flowchart of an operation of an X-ray imaging apparatus of FIG. 25. Referring to FIG. 29, when the object 200 is inserted in the holder 145 and preparation of X-ray imaging is completed, the light-emitting unit 1850 is driven to emit the light L. The light-receiving unit 1860 detects the light L of the light-emitting unit 1850 and thus the size of the object 200 is determined (operation S1910). In operation S1920, only the X-ray generation units 300 of the linear X-ray generator 150 that correspond to the area where the object 200 is disposed are activated, so that the X-ray is radiated only to the X-ray radiation field 1871 that corresponds to the size of the object 200 (operation S1930). As such, since the X-ray generation units 300 corresponding to the outer area 1872 of the X-ray radiation field 1871 are not driven, an X-ray radiation dose may be reduced and driving power of the linear X-ray generator 150 may be reduced.

The determining of a radiation field may be performed before the X-ray imaging is performed. In other words, when the object 200 is inserted in the holder 145 and the preparation of the X-ray imaging is completed, the light-emitting unit 1850 and the light-receiving unit 1860 are driven and rotated so that the entire size of the object 200 is scanned and then X-ray imaging may be performed for only the radiation field.

In another example, the determining of the radiation field may be performed simultaneously with the X-ray imaging. As described above, the X-ray imaging is performed while the linear X-ray generator 150 and the linear X-ray detector 160 rotate around the holder 145. Accordingly, while the linear X-ray generator 150 and the linear X-ray detector 160 rotate around the holder 145 and simultaneously the X-ray imaging is performed, the light-emitting unit 1850 and the light-receiving unit 1860 are continuously or discontinuously driven to determine the X-ray radiation field. Accordingly, an X-ray radiation range may be determined in real time.

The above-described X-ray radiation field determination operation may be implemented before or at the same time as performing X-ray imaging (operation S1130), in the operation of the X-ray imaging apparatus described above with reference to FIG. 16.

Figure 30:
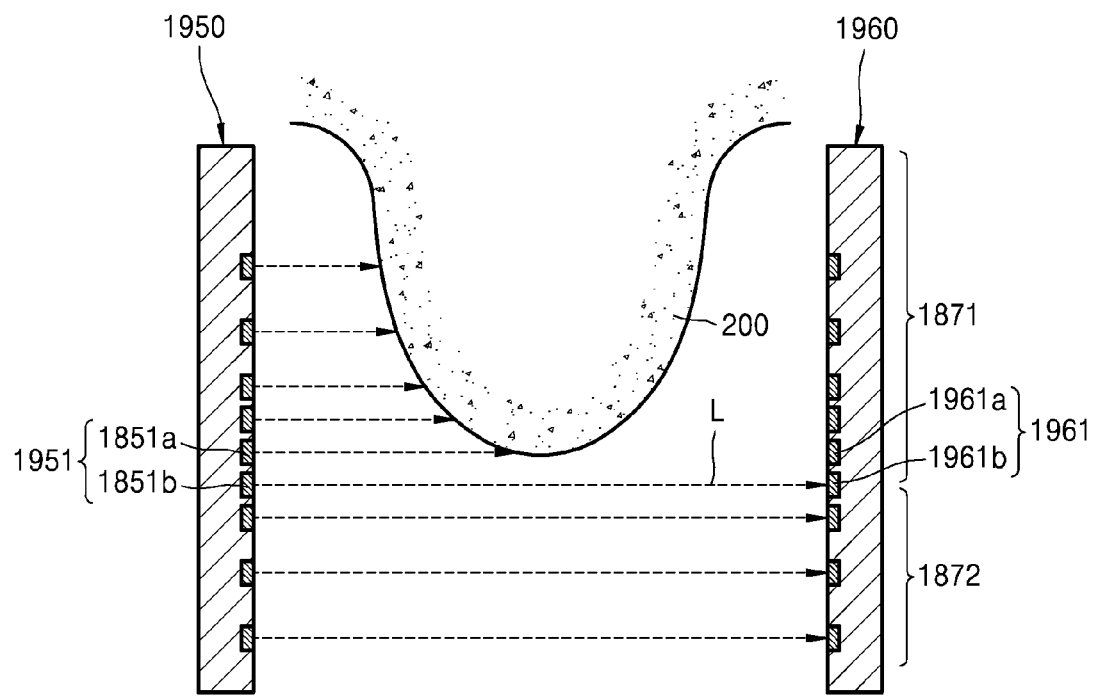
FIG. 30 illustrates an arrangement of light-emitting elements of a light-emitting unit and light-receiving elements of a light-receiving unit according to an exemplary embodiment.

Although the light-emitting elements 1851 and the light-receiving elements 1861 are described to be arranged at identical intervals, an exemplary embodiment is not limited thereto. FIG. 30 illustrates an arrangement of a plurality of light-emitting elements 1951 of a light-emitting unit 1950 and a plurality of light-receiving elements 1961 of a light-receiving unit 1960, according to an exemplary embodiment. As illustrated in FIG. 30, the light-emitting elements 1951 and the light-receiving elements 1961 of the light-receiving unit 1960 may be irregularly arranged. The size or shape of the object, that is, the breast of a patient, may be averaged. Accordingly, considering the average size of the object, the light-emitting elements 1951 and the light-receiving elements 1961 corresponding thereto may be densely arranged in the vicinity of an area where the end portion of the average object is placed, whereas the light-emitting elements 1951 and the light-receiving elements 1961 corresponding thereto may be sparsely arranged in the other area. In other words, the light-receiving elements 1961 disposed in the vicinity of a boundary between a light-receiving element 1961a that does not detect the light L and a light-receiving element 1961b that adjoins the light-receiving element 1961a and detects the light L, among the light-receiving elements 1961 that are vertically arranged, are densely arranged, whereas the light-emitting elements 1951 and the light-receiving elements 1961 are sparsely arranged. As such, according to the above arrangement of the light-emitting elements 1951 and the light-receiving elements 1961, a more accurate size of the average object may be determined and, as the number of parts in use decreases, manufacturing costs may be reduced.

Figure 31:
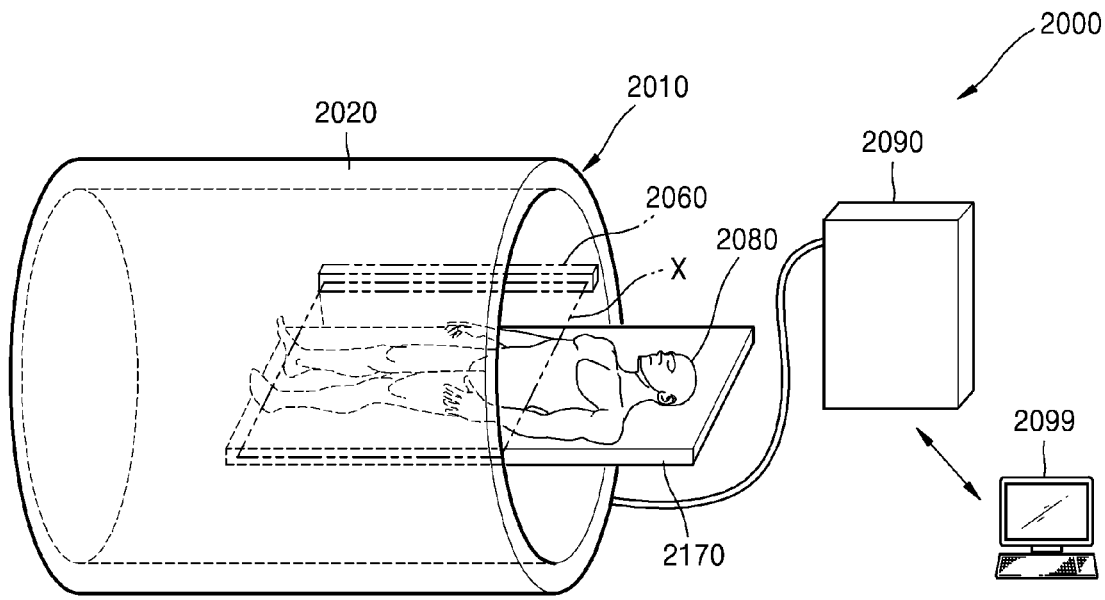
FIG. 31 illustrates a schematic structure of an X-ray imaging apparatus according to an exemplary embodiment.
Figure 32:
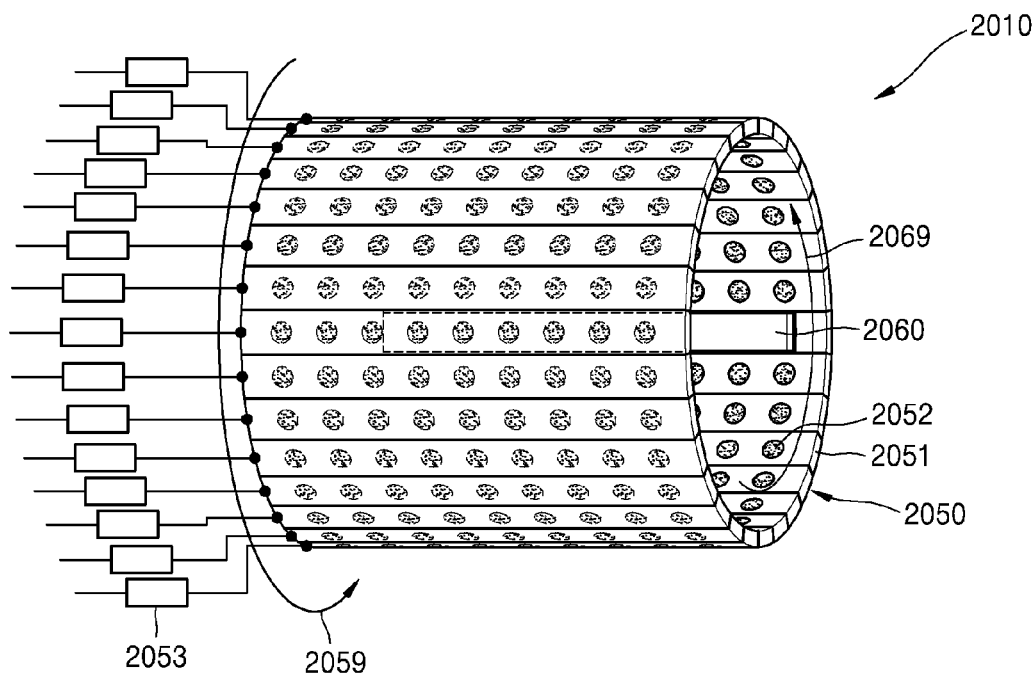
FIG. 32 schematically illustrates a cylindrical X-ray generator assembly employed in the X-ray imaging apparatus of FIG. 31.

FIG. 31 illustrates a schematic structure of an X-ray imaging apparatus 2000 according to an exemplary embodiment. FIG. 32 schematically illustrates a cylindrical X-ray generator assembly 2050 employed in the X-ray imaging apparatus 2000 of FIG. 31.

Referring to FIGS. 31 and 32, the X-ray imaging apparatus 2000 includes a main assembly 2010 where X-ray imaging is performed and a control apparatus 2090 controlling the main assembly 2010. The main assembly 2010 includes a housing 2020 having a cylindrical shape and the cylindrical X-ray generator assembly 2050 and a linear X-ray detector 2060 which are provided in the housing 2020. The X-ray imaging apparatus 2000 according to an exemplary embodiment may perform X-ray imaging on the entire body or a particular portion of a patient (hereinafter, referred to as the object).

Figure 33:
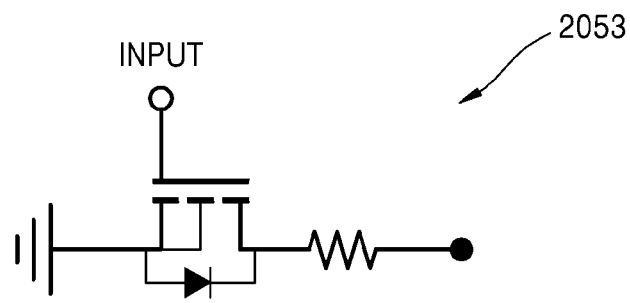
FIG. 33 illustrates an example of a switch circuit used in the cylindrical X-ray generator assembly of FIG. 32.

Referring to FIG. 32, the cylindrical X-ray generator assembly 2050 has a structure in which a plurality of X-ray generation units 2052 are two-dimensionally arranged on an inner circumferential surface of a cylinder. The cylindrical X-ray generator assembly 2050 may be sequentially driven along a circumferential direction 2059. The cylindrical X-ray generator assembly 2050 may be understood as a structure in which a plurality of linear X-ray generators 2051 that are independently switched are arranged around the circumferential direction 2059. Each linear X-ray generator 2051 may include the X-ray generation units 2052 that are linearly arranged. The X-ray generation units 2052 are provided to radiate all X-rays perpendicularly to the circumferential direction 2059 toward a center axis of the cylindrical X-ray generator assembly 2050. The linear X-ray generator 2051 and the X-ray generation units 2052 may respectively correspond to the linear X-ray generator 150 and the X-ray generation units 300 that are described above. A switching circuit 2053 may be individually provided for each linear X-ray generator 2051. The switching circuit 2053 may be a circuit using a switching operation of a transistor as illustrated in FIG. 33. The switching circuit of FIG. 33 is a mere example and a variety of appropriate switching circuits may be used. When input signals are sequentially applied to switching circuits provided in the circumferential direction 2059 of the cylindrical X-ray generator assembly 2050, power is applied to a corresponding one of the linear X-ray generators 2051 and thus the linear X-ray generators 2051 are sequentially driven in the circumferential direction 2059 of the cylindrical X-ray generator assembly 2050.

Figure 34:
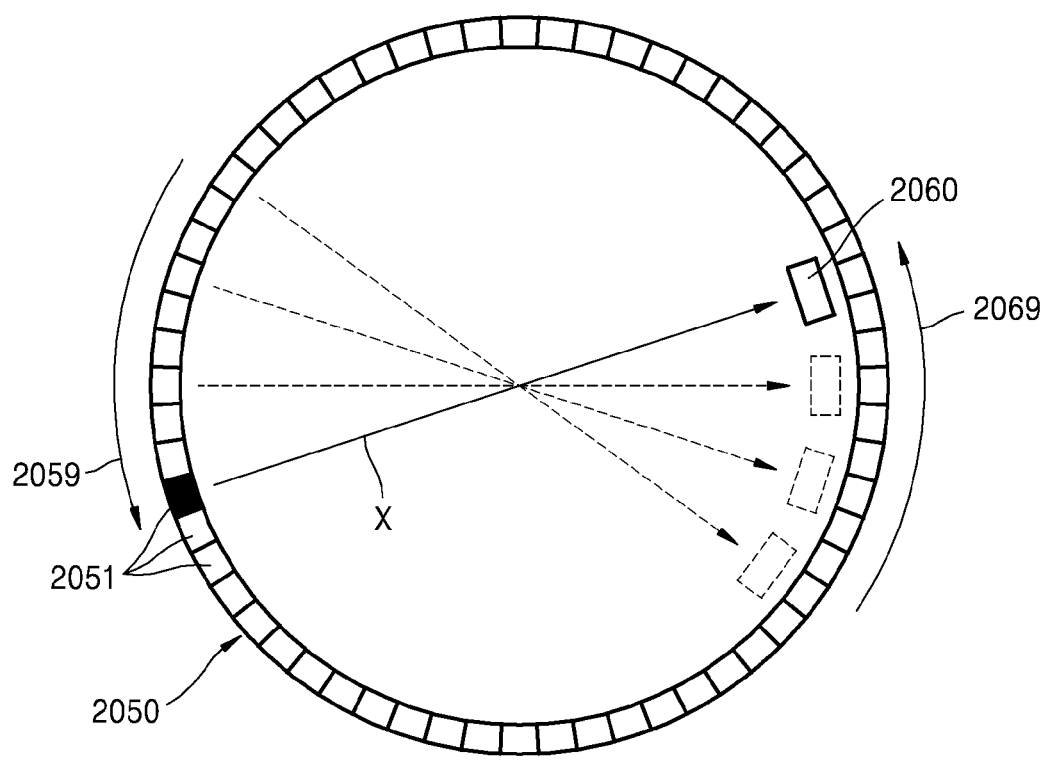
FIG. 34 illustrates an operation of the X-ray imaging apparatus of FIG. 31.

The linear X-ray detector 2060 is provided to be capable of rotating along the circumference of the housing 2020. The linear X-ray detector 2060 may be disposed inside the cylindrical X-ray generator assembly 2050. The linear X-ray detector 2060 may be driven to be rotated by a device known to those skilled in the art. Referring to FIG. 34, when the linear X-ray generators 2051 sequentially radiate X-rays along the circumferential direction 2059 of the cylindrical X-ray generator assembly 2050, the linear X-ray detector 2060 rotates in a direction 2069 to a position opposite to a corresponding one of the linear X-ray generators 2051 that radiates an X-ray with respect to the center axis and detects the X-rays that are sequentially radiated. When all of the linear X-ray generators 2051 are sequentially driven along the circumferential direction 2059, the linear X-ray detector 2060 rotates by 360° accordingly.

Only some of the linear X-ray generators 2051 may be sequentially driven. In this case, the linear X-ray detector 2060 may rotate within an angular range corresponding thereto. In some cases, when an X-ray X is radiated by any one of the linear X-ray generators 2051 of the cylindrical X-ray generator assembly 2050, the linear X-ray detector 2060 may rotate within an angle and detect the X-ray in the vicinity of a position opposite to the corresponding linear X-ray generators 2051. As such, since the X-ray is radiated to the object at a varying angle, an X-ray signal detected by the linear X-ray detector 2060 includes angular information and tomographic information. Accordingly, a tomographic image or a tomosynthesis image may be obtained based on the obtained angular information and tomographic information. Also, a tomographic image may be reconstructed in two or three dimensions based on the obtained angular information and tomographic information.

Figure 35:
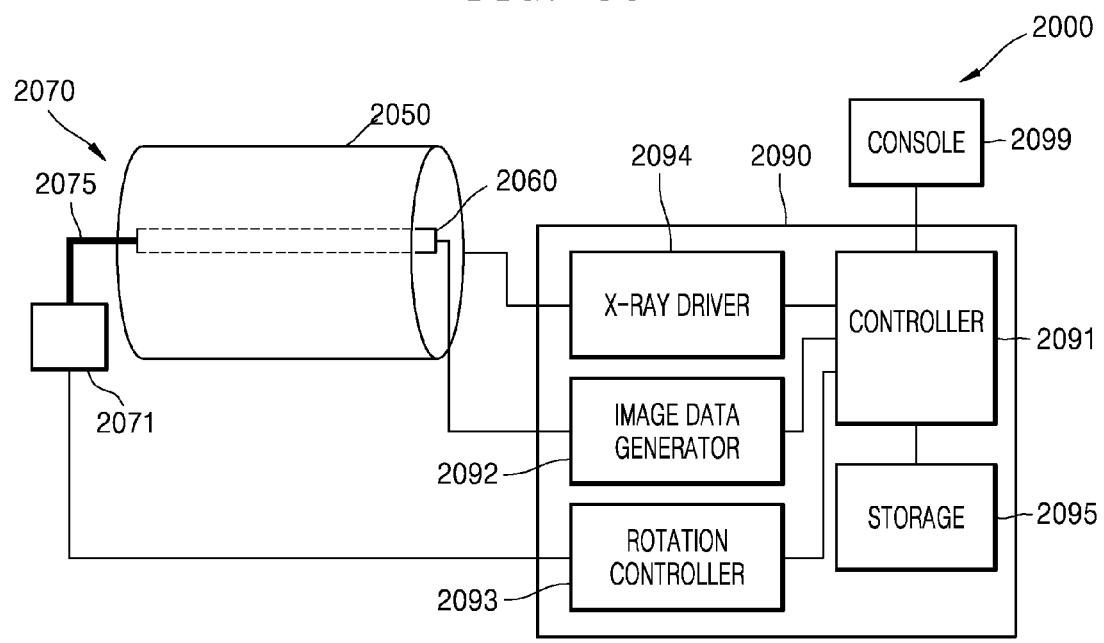
FIG. 35 is a schematic block diagram of the X-ray imaging apparatus of FIG. 31.

Since only the linear X-ray detector 2060 that is relatively light is mechanically driven and rotated in the X-ray imaging apparatus 2000 according to an exemplary embodiment, a relatively small load is applied to a rotation driver 2070 of FIG. 35 and thus a mechanical structure of the rotation driver 2070 may be greatly simplified.

FIG. 35 is a schematic block diagram of the X-ray imaging apparatus 2000 of FIG. 31. Referring to FIG. 35, the X-ray imaging apparatus 2000 according to an exemplary embodiment includes a cylindrical X-ray generator assembly 2050, a linear X-ray detector 2060, the rotation driver 2070 driving the linear X-ray detector 2060 to rotate, and a control apparatus 2090 controlling the above elements.

The control apparatus 2090 may include a controller 2091, an image data generator 2092, a rotation controller 2093, an X-ray driver 2094, and a storage 2095. The control apparatus 2090 may receive an input of a command about X-ray imaging from a user through a console 2099. The information about a command to drive the cylindrical X-ray generator assembly 2050, a command to activate the linear X-ray detector 2060, a command to rotationally drive the linear X-ray detector 2060, a command to control a parameter to change a spectrum of an X-ray, etc., which are input by a user, is transferred to the controller 2091. The controller 2091 controls the elements in the control apparatus 2090 according to the user's command.

The image data generator 2092 receives electric signals corresponding to the X-ray detected by the linear X-ray detector 2060. The image data generator 2092 generates digital sectional data containing information about a section of the object, from the received electric signals. One-time radiation of an X-ray by any one linear X-ray generator 2051 of the cylindrical X-ray generator assembly 2050 generates one section linear data containing information about a section of the object.

A plurality of pieces of section data about different sections of the object are generated when the X-ray is radiated many times by varying the positions of the linear X-ray generators 2051 of the cylindrical X-ray generator assembly 2050. When the pieces of section data are accumulated into adjoining section data, 3D volume data representing the object in three dimensions may be generated.

The rotation controller 2093 controls the rotation driver 2070 to drive the cylindrical X-ray generator assembly 2050 to rotate. The rotation driver 2070 includes a drive motor 2071 and a power transfer unit 2075 controlling a driving force generated by the drive motor 2071 and transferring the controlled driving force to the linear X-ray detector 2060.

The X-ray driver 2094 sequentially controls the linear X-ray generators 2051 of the cylindrical X-ray generator assembly 2050. Also, the X-ray driver 2094 may individually or collectively control X-ray radiation strength of the X-ray generation units 2052 of the linear X-ray generators 2051.

The storage 2095 may store the section data and/or the 3D volume data generated by the image data generator 2092. The storage 2095 may transmit to the console 2099 the stored section data or 3D volume data on a user's request.

Figure 36:
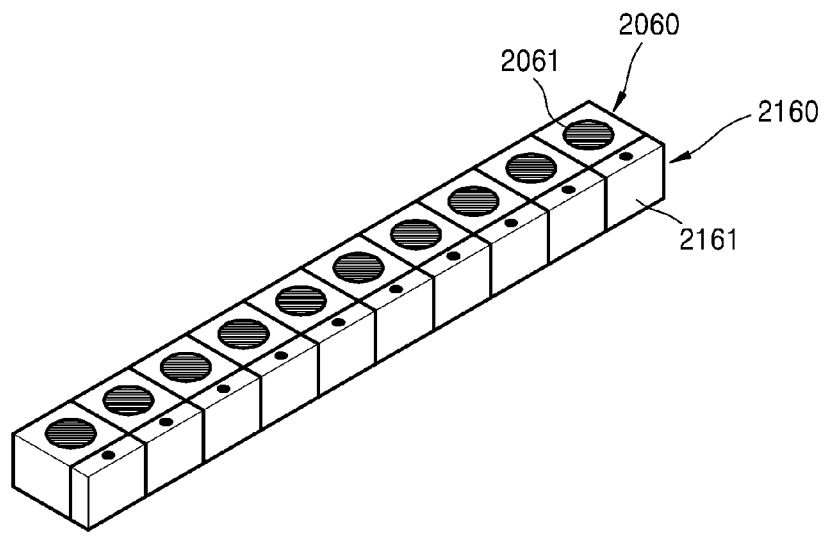
FIG. 36 illustrates a radiation field detector employed in an X-ray imaging apparatus according to an exemplary embodiment.

FIG. 36 illustrates a radiation field detector 2160 employed in an X-ray imaging apparatus, according to an exemplary embodiment, that may be additionally provided to the linear X-ray detector 2060 of the X-ray imaging apparatus 2000 that is described with reference to FIGS. 31 to 35.

Referring to FIG. 36, the radiation field detector 2160 may extend in a lengthwise direction and may be provided at one side of the linear X-ray detector 2060 which includes detection units 2061. The radiation field detector 2160 may include a plurality of light sensors 2161 that are linearly arranged. The light sensors 2161 may be arranged at an identical interval. Alternatively, the light sensors 2161 may be arranged densely in a section corresponding to an area that is a boundary of a radiation field and sparsely in the other section.

The light sensor 2161 is a light sensor detecting luminosity. The radiation field detector 2160 may be integrally combined with the linear X-ray detector 2060 and rotate along the circumference of the housing 2020 of FIG. 31 with the linear X-ray detector 2060. The linear X-ray detector 2060 and the radiation field detector 2160 may be disposed on an inner wall surface of the housing 2020. In this case, the inner wall surface of the housing 2020 may be formed of a transparent material so that the light sensor of the radiation field detector 2160 may detect luminosity. In some cases, the linear X-ray detector 2060 and the radiation field detector 2160 may be disposed outside the inner wall surface of the housing 2020.

When the object is located inside the housing 2020, an area where the object is located is different than an area where the object in terms of luminosity detected by the radiation field detector 2160 according to a difference in the distance from the radiation field detector 2160 and shadow generated by the object. Accordingly, when the radiation field detector 2160 rotates along the circumference of the housing 2020 with the linear X-ray detector 2060, approximate position and size of the object may be detected by the radiation field detector 2160. The control apparatus 2090 of FIG. 31 may determine an X-ray radiation field based on the approximate position and size of the object detected by the radiation field detector 2160.

As described above, since the X-ray generation units 2052 of the cylindrical X-ray generator assembly 2050 may be individually controlled, only the X-ray generation units 2052 corresponding to the X-ray radiation field are activated. Accordingly, an X-ray radiation dose to the object may be reduced and also the driving power of the cylindrical X-ray generator assembly 2050 may be reduced.

The determining of the X-ray radiation field may be performed before the X-ray imaging is performed. In other words, when the object enters the housing 2020 and preparation of the X-ray imaging is completed, the radiation field detector 2160 is driven and rotated along the circumference of the housing 2020 to scan the total size of the object and then X-ray imaging is performed on a target object only.

In another case, the determining of the X-ray radiation field may be performed at the same time with the X-ray imaging. As described above, since the X-ray imaging is performed while the linear X-ray detector 2060 rotates along the circumference of the housing 2020, during the X-ray imaging, the radiation field detector 2160 is continuously or discontinuously driven to determine the X-ray radiation field. Accordingly, an X-ray radiation range may be determined in real time.

Figure 37:
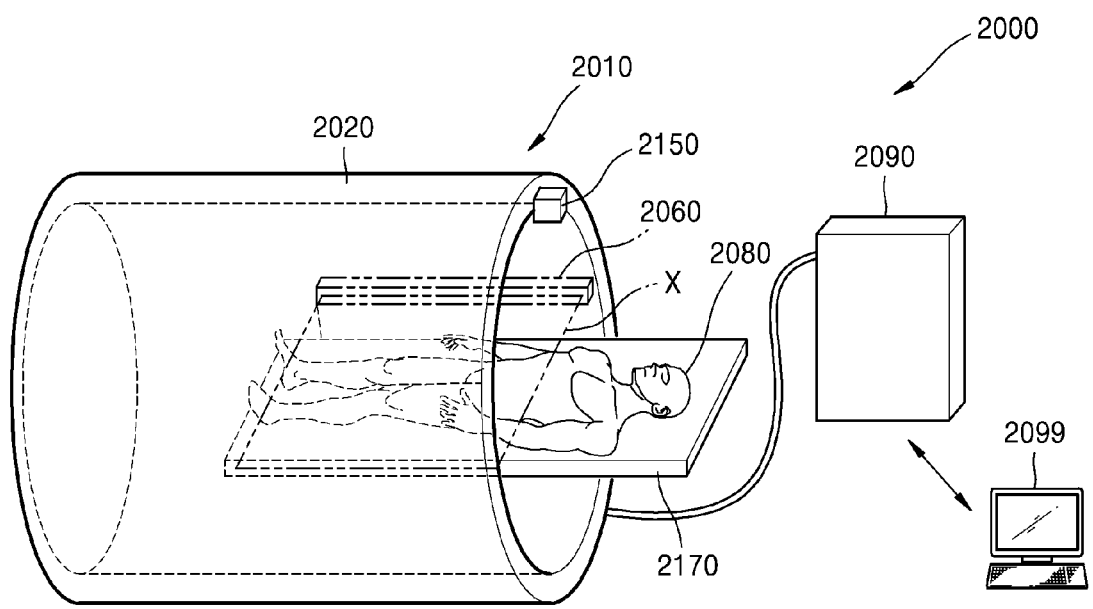
FIG. 37 illustrates a schematic structure of an X-ray imaging apparatus according to an exemplary embodiment.

FIG. 37 illustrates a schematic structure of an X-ray imaging apparatus 2000, according to an exemplary embodiment, which additionally includes a radiation field detector 2150.

The radiation field detector 2150 may be a sensor that is provided at an upper portion of an entrance of the housing 2020 and recognizes a particular portion of a table 2170 or a particular portion of a patient 2080 when the patient 2080 lying on the table 2170 enters the housing 2020. A marker may be attached on the particular portion of the table 2170 or a radiation target field of the patient 2080. The radiation field detector 2150 may be a proximity sensor, an image sensor, etc. When the patient enters the housing 2020 by lying on the table 2170, the radiation field detector 2150 recognizes the particular portion of the table 2170 or the particular portion of the patient. The position of the patient may be specified by integrating an entering velocity of the table 2170 for an entering time by using the position recognized by the radiation field detector 2150 as a reference point. When the X-ray radiation field of the patient is specified, a user may activate only the X-ray generation units 2052 corresponding to the X-ray radiation field through the control apparatus 2090. Accordingly, an X-ray radiation dose to an object may be reduced and also the driving power of the cylindrical X-ray generator assembly 2050 may be reduced.

As described above, in the device and method for controlling an X-ray radiation field of an X-ray imaging apparatus according to one or more of exemplary embodiments, a radiation exposure to a patient may be reduced as compared to a related art X-ray imaging apparatus. Also, an image may be rapidly obtained as compared to the related art linear detector type X-ray imaging apparatus.

Also, when the X-ray imaging apparatus is used as a breast imaging apparatus, an operation of pressing the breast of a patient is not needed and thus the patient is not in pain due to breast compression. Since the steps and frequencies of imaging may be remarkably reduced, as compared to the related art imaging requiring both of general imaging of RCC, RMLO, LCC, and LMLO and tomosynthesis imaging, a workflow may be simplified and a patient's radiation dose may be reduced.

Also, when a limited area is to be X-ray imaged, an X-ray radiation field is manually or automatically set so that X-ray may be radiated in a particular area only by automatically controlling turning on/off of an X-ray source of the X-ray generator, thereby reducing a radiation dose to the patient. Furthermore, when the X-ray imaging apparatus is used as a breast imaging apparatus, in consideration that the sizes of a breast are different for patients, when the breast of a patient is inserted in a breast imaging apparatus, the breast size of a patient is automatically recognized through a detection sensor attached next to the X-ray generator. The on/off of the X-ray source is automatically controlled so that an X-ray may be radiated only to the recognized size of breast, thereby reducing radiation to the patient. Also, since the X-ray radiation field is controlled by automatically recognizing a imaging area of the breast of a patient, a imaging time may be reduced.

The foregoing exemplary embodiments and advantages are merely exemplary and are not to be construed as limiting. The present teaching can be readily applied to other types of apparatuses. The description of the exemplary embodiments is intended to be illustrative, and not to limit the scope of the claims, and many alternatives, modifications, and variations will be apparent to those skilled in the art. For example, each single component may be separated into multiple components which are then separately implemented. Also, separated components may be combined together and implemented as a single component.

What is claimed is:

1. An apparatus for controlling an X-ray radiation field of an X-ray imaging apparatus comprising an X-ray generator and an X-ray detector arranged opposite to the X-ray generator, the apparatus comprising:
    a light-emitting unit configured to emit light and disposed adjacent to one of the X-ray generator and the X-ray detector;
    a light-receiving unit configured to detect the light emitted by the light-emitting unit and disposed adjacent to the other one of the X-ray generator and the X-ray detector; and
    a controller configured to control setting of the X-ray radiation field based on the detected light and to control driving of X-ray generation units of the X-ray generator that correspond to the set X-ray radiation field, to emit an X-ray,
    wherein the light-emitting unit comprises light-emitting elements,
    wherein the light-emitting elements have a fixed relative position with respect to each other, and
    wherein the light-emitting elements have a fixed relative position with respect to the one of the X-ray generator and the X-ray detector during controlling the X-ray radiation field of the X-ray imaging apparatus.

2. The apparatus of claim 1, wherein X-ray generation units are linearly arranged, and
    the light-emitting elements are arranged in a same direction as a direction in which the X-ray generation units are linearly arranged.

3. The apparatus of claim 1, wherein the light-emitting elements comprise at least one among a light-emitting diode, an organic light-emitting diode, a laser diode, and a lamp.

4. The apparatus of claim 2, wherein the light-emitting elements emit at least one among visible rays and infrared rays.

5. The apparatus of claim 1, wherein the X-ray generation units are linearly arranged, and
    the light-receiving unit has a linear light detection surface extending in a same direction as a direction in which the X-ray generation units are linearly arranged.

6. The apparatus of claim 1, wherein the X-ray generation units are linearly arranged, and
    the light-receiving unit comprises light-receiving elements having a fixed relative position with respect to each other that are arranged in a same direction as a direction in which the X-ray generation units are linearly arranged.

7. The apparatus of claim 6, wherein the light-receiving elements comprise at least one among a photodiode, a phototransistor, and an image sensor.

8. The apparatus of claim 1, wherein the light-emitting unit is provided at a side surface of one of the X-ray generator and the X-ray detector, and
    the light-receiving unit is provided at a side surface of the other one of the X-ray generator and the X-ray detector.

9. The apparatus of claim 8, wherein the light-emitting unit is attached to the side surface of the X-ray generator, the side surface being a leading surface with respect to a rotation direction in which the X-ray generator and the X-ray detector rotate.

10. The apparatus of claim 8, wherein the light-receiving unit is attached to the side surface of the X-ray detector, the side surface being a leading surface with respect to a rotation direction in which the X-ray generator and the X-ray detector rotate.

11. A method of controlling an X-ray radiation field of an X-ray imaging apparatus comprising an X-ray generator and an X-ray detector arranged opposite to the X-ray generator, the method comprising:
    emitting light from a light-emitting unit comprising a plurality of light-emitting elements, the light-emitting unit disposed adjacent to one of the X-ray generator and the X-ray detector toward the other one of the X-ray generator and the X-ray detector, wherein the plurality of light-emitting elements have a fixed relative position with respect to each other;
    detecting the emitted light using a light-receiving unit comprising a plurality of light-receiving elements, the light-receiving unit disposed adjacent to the other one of the X-ray generator and the X-ray detector, wherein the plurality of light-receiving elements have a fixed relative position with respect to each other;
    setting the X-ray radiation field based on the detected light; and controlling driving of X-ray generation units of the X-ray generator that correspond to the set X-ray radiation field, to emit an X-ray, and wherein the plurality of light-emitting elements have a fixed relative position with respect to the one of the X-ray generator and the X-ray detector during controlling the X-ray radiation field of the X-ray imaging apparatus.

12. The method of claim 11, wherein the X-ray generation units are linearly arranged, and the emitting the light comprises:

emitting a linear light having a linear beam section that extends continuously or discontinuously in a same direction as a direction in which the X-ray generation units are linearly arranged.

13. The method of claim 11, wherein the setting the X-ray radiation field comprises:

setting the X-ray radiation field as an area obtained by adding a preset width to an outer edge, to extend the X-ray radiation field into an area where the light is not detected.

14. The method of claim 11, wherein the X-ray generation units that are linearly arranged and the method further comprises:

rotating the X-ray generator and the X-ray detector, which face each other, around a rotational axis that is between the X-ray generator and the X-ray detector and parallel to a direction in which the X-ray generation units are linearly arranged.

15. The method of claim 11, wherein the light-emitting unit is attached to a side surface of the X-ray generator, the side surface being a leading surface in a rotation direction in which the X-ray generator and the X-ray detector rotate, and configured to emit light prior to emission of the X-ray by the X-ray generator.

16. The method of claim 11, wherein the light-receiving unit is attached to a side surface of the X-ray detector, the side surface being a leading surface in a rotation direction in which the X-ray generator and the X-ray detector rotate, and configured to receive light prior to detection of the X-ray by the X-ray detector.

17. An X-ray imaging apparatus comprising:

a cylindrical assembly comprising:

an X-ray generator and an X-ray detector arranged opposite to the X-ray generator, a light emitter configured to emit light and disposed adjacent to one of the X-ray generator and the X-ray detector, the light emitting comprising a plurality of light-emitting elements, and a light receiver configured to detect the light and disposed adjacent to the other one of the X-ray generator and the X-ray detector, the light receiver comprising a plurality of light-receiving elements, wherein the light emitter and the light receiver are arranged in parallel and opposite to one another along a circumference of the cylindrical assembly and have an elongated linear shape that extends in a direction parallel to a central axis of the cylindrical assembly; and a controller configured to control setting of an X-ray radiation field based on the detected light, wherein the plurality of light-emitting elements have a fixed relative position with respect to each other, wherein the plurality of light-receiving elements have a fixed relative position with respect to each other, and wherein the plurality of light-emitting elements have a fixed relative position with respect to the one of the X-ray generator and the X-ray detector during controlling the X-ray radiation field of the X-ray imaging apparatus.

18. The X-ray imaging apparatus of claim 17, wherein:

the X-ray generator is configured to radiate X-rays within the X-ray radiation field and is adjacent to the light emitter; and the X-ray detector is configured to receive the X-rays and is adjacent to the light receiver.

19. The X-ray imaging apparatus of claim 17, wherein:

the X-ray generator is configured to radiate X-rays within the X-ray radiation field and is adjacent to the light receiver; and the X-ray detector is configured to receive the X-rays and is adjacent to the light emitter.

20. The apparatus of claim 1, wherein the light-emitting elements are arranged in an array disposed in a supporting member disposed adjacent the X-ray generator.

\* \* \* \* \*